US008318181B2

(12) United States Patent
Edelson et al.

(10) Patent No.: US 8,318,181 B2
(45) Date of Patent: Nov. 27, 2012

(54) BOTULINUM NANOEMULSIONS

(75) Inventors: Jonathan Edelson, Scarsdale, NY (US);
Robert J. Nicolosi, Nashua, NH (US)

(73) Assignee: University of Massachusetts Lowell,
Lowell, MA (US)

( * ) Notice: Subject to any disclaimer, the term of this patent is extended or adjusted under 35 U.S.C. 154(b) by 1499 days.

(21) Appl. No.: 11/607,436

(22) Filed: Dec. 1, 2006

(65) Prior Publication Data

US 2012/0164182 A1 Jun. 28, 2012

Related U.S. Application Data

(60) Provisional application No. 60/741,139, filed on Dec. 1, 2005.

(51) Int. Cl.
*A61K 39/40* (2006.01)
*A61K 39/08* (2006.01)
*A61K 9/66* (2006.01)

(52) U.S. Cl. .................. 424/239.1; 424/167.1; 424/455

(58) Field of Classification Search .................. None
See application file for complete search history.

(56) References Cited

U.S. PATENT DOCUMENTS

| 4,533,254 | A | 8/1985 | Cook et al. |
| 4,908,154 | A | 3/1990 | Cook et al. |
| 5,152,923 | A | 10/1992 | Weder et al. |
| 5,374,614 | A | 12/1994 | Behan et al. |
| 5,401,243 | A | 3/1995 | Borodic |
| 5,502,045 | A | 3/1996 | Miettinen et al. |
| 5,510,118 | A | 4/1996 | Bosch et al. |
| 5,576,016 | A | 11/1996 | Amselem et al. |
| 5,629,021 | A | 5/1997 | Wright |
| 5,651,991 | A | 7/1997 | Sugiyama et al. |
| 5,652,274 | A | 7/1997 | Martin |
| 5,670,484 | A | 9/1997 | Binder |
| 5,672,358 | A | 9/1997 | Tabibi et al. |
| 5,753,241 | A | 5/1998 | Ribier et al. |
| 5,766,605 | A | 6/1998 | Sanders et al. |
| 5,851,452 | A | 12/1998 | Vallet Mas et al. |
| 5,858,410 | A | 1/1999 | Muller et al. |
| 5,925,341 | A | 7/1999 | Cervantes et al. |
| 5,932,562 | A | 8/1999 | Ostlund, Jr. |
| 5,994,414 | A | 11/1999 | Franco et al. |
| 6,007,856 | A | 12/1999 | Cox et al. |
| 6,039,936 | A | 3/2000 | Restle et al. |
| 6,165,500 | A | 12/2000 | Cevc |
| 6,224,853 | B1 | 5/2001 | Steel et al. |
| 6,265,180 | B1 | 7/2001 | Zuelli et al. |
| 6,274,150 | B1 | 8/2001 | Simonnet et al. |
| 6,312,708 | B1 | 11/2001 | Donovan |
| 6,358,917 | B1 | 3/2002 | Carruthers et al. |
| 6,387,411 | B2 | 5/2002 | Bruce et al. |
| 6,429,189 | B1 | 8/2002 | Borodic |
| 6,558,941 | B2 | 5/2003 | Zuelli et al. |
| 6,573,241 | B1 | 6/2003 | Bigalke et al. |
| 6,589,588 | B1 | 7/2003 | Wester et al. |
| 6,623,780 | B1 | 9/2003 | Stevens et al. |
| 6,632,440 | B1 | 10/2003 | Quinn et al. |
| 6,670,322 | B2 | 12/2003 | Goodnough et al. |
| 6,688,311 | B2 | 2/2004 | Hanin |
| 6,720,001 | B2 | 4/2004 | Chen et al. |
| 6,835,395 | B1 | 12/2004 | Semple |
| 6,861,066 | B2 | 3/2005 | Van de Casteele |
| 6,869,610 | B2 | 3/2005 | Aoki et al. |
| 6,902,737 | B2 | 6/2005 | Quemin |
| 6,939,852 | B2 | 9/2005 | Graham |
| 6,974,578 | B1 | 12/2005 | Aoki et al. |
| 6,974,579 | B2 | 12/2005 | Brin et al. |
| 7,001,602 | B2 | 2/2006 | Schmidt |
| RE39,086 | E | 5/2006 | Carruthers et al. |
| 7,226,605 | B2 | 6/2007 | Suskind et al. |
| 7,228,259 | B2 | 6/2007 | Freund |
| 7,255,865 | B2 | 8/2007 | Walker |
| 7,384,918 | B2 | 6/2008 | Graham |
| 7,507,419 | B2 | 3/2009 | Coleman, III |
| 7,763,663 | B2 | 7/2010 | McCarthy et al. |
| 2002/0015721 | A1 | 2/2002 | Simonnet et al. |
| 2002/0048596 | A1 | 4/2002 | Cevc |
| 2002/0098215 | A1 | 7/2002 | Douin et al. |
| 2002/0107199 | A1 | 8/2002 | Walker |
| 2002/0155084 | A1 | 10/2002 | Roessler et al. |
| 2002/0165179 | A1 | 11/2002 | Baker |
| 2003/0072801 | A1 | 4/2003 | Curatolo et al. |

(Continued)

FOREIGN PATENT DOCUMENTS

CA 2494473 4/2005

(Continued)

OTHER PUBLICATIONS

Keen et al (Plastic and Reconstructive Surgery, Jul. 1994).*
International Search Report for Application No. PCT/US06/46236, dated Jun. 17, 2008.
International Search Report for Application No. PCT/US06/26918, dated Jun. 19, 2008.
Badea et al., "In vivo cutaneous interferon-γ gene delivery using novel dicationic (gemini) surfactant-plasmid complexes", The Journal of Gene Medicine, 7:1200-1214 (2005).
Bos and Meinardi, "The 500 Dalton rule for the skin penetration of chemical compounds and drugs," Exp. Dermatol., 9:165-169 (2000).
Chen et al., "Transdermal protein delivery by a coadministered peptide identified via phage array," Nature Biotechnology, 24(4):455-459 (2006).

(Continued)

*Primary Examiner* — Nita M Minnifield
(74) *Attorney, Agent, or Firm* — McCarter & English, LLP; Danielle Herritt; Marcie B. Clarke

(57) ABSTRACT

The embodiment described herein are related nanoemulsions comprising botulinum toxins. In one embodiment, the nanoemulsions are prepared by high pressure microfluidization and comprise a particle size distribution exclusively between 10 and 300 nm. The nanoemulsions contemplated by the present invention are useful for the cosmetic and medical treatment of muscular contracture states. For example, botulinum toxin may relax facial muscles such that skin wrinkles become smoother and less noticeable. Further, the present invention contemplates a cosmetic formulation that may be self-administered, for example, in the privacy of one's home and without medical supervision.

9 Claims, 3 Drawing Sheets

U.S. PATENT DOCUMENTS

| | | | |
|---|---|---|---|
| 2003/0108597 A1 | 6/2003 | Chancellor et al. |
| 2003/0113349 A1 | 6/2003 | Coleman |
| 2003/0138465 A9 | 7/2003 | Douin et al. |
| 2003/0194412 A1 | 10/2003 | Baker et al. |
| 2003/0206955 A1 | 11/2003 | Sonneville-Aubrun et al. |
| 2003/0224020 A1 | 12/2003 | Zabudkin et al. |
| 2004/0003324 A1 | 1/2004 | Uhlig et al. |
| 2004/0005370 A1 | 1/2004 | Breton |
| 2004/0009180 A1 | 1/2004 | Donovan |
| 2004/0009936 A1 | 1/2004 | Tang et al. |
| 2004/0033202 A1 | 2/2004 | Cooper et al. |
| 2004/0033241 A1 | 2/2004 | Donovan |
| 2004/0037853 A1 | 2/2004 | Borodic |
| 2004/0048836 A1 | 3/2004 | Wilmott |
| 2004/0081688 A1 | 4/2004 | Del Curto et al. |
| 2004/0115159 A1 | 6/2004 | Tadlock et al. |
| 2004/0115727 A1 | 6/2004 | Steward et al. |
| 2004/0126397 A1 | 7/2004 | Aoki et al. |
| 2004/0127661 A1 | 7/2004 | Kaspar et al. |
| 2004/0151741 A1 | 8/2004 | Borodic |
| 2004/0229038 A1 | 11/2004 | Cooper et al. |
| 2004/0258758 A1 | 12/2004 | Gustow et al. |
| 2005/0048088 A1 | 3/2005 | Zulli et al. |
| 2005/0074461 A1 | 4/2005 | Donovan |
| 2005/0074466 A1 | 4/2005 | Suskind et al. |
| 2005/0079131 A1 | 4/2005 | Lanza et al. |
| 2005/0096340 A1 | 5/2005 | Zhang |
| 2005/0123897 A1 | 6/2005 | Cevc et al. |
| 2005/0142150 A1 | 6/2005 | Graham |
| 2005/0147688 A1 | 7/2005 | Russell |
| 2005/0175636 A1 | 8/2005 | Donovan |
| 2005/0184275 A1 | 8/2005 | Mora-Gutierrez et al. |
| 2005/0196414 A1 | 9/2005 | Dake et al. |
| 2005/0208083 A1 | 9/2005 | Annis |
| 2005/0214325 A1 | 9/2005 | David |
| 2005/0226842 A1 | 10/2005 | Douin et al. |
| 2005/0249686 A1 | 11/2005 | Pataut et al. |
| 2005/0261632 A1 | 11/2005 | Xu |
| 2006/0018931 A1 | 1/2006 | Taylor |
| 2006/0057165 A1 | 3/2006 | Dimitrakoudis et al. |
| 2006/0073208 A1 | 4/2006 | First |
| 2006/0093624 A1 | 5/2006 | Graham |
| 2006/0153876 A1 | 7/2006 | Sanders |
| 2006/0153877 A1 | 7/2006 | Kozaki et al. |
| 2006/0165657 A1 | 7/2006 | Bernasconi et al. |
| 2006/0182767 A1 | 8/2006 | Borodic |
| 2006/0188525 A1 | 8/2006 | Donovan |
| 2007/0036831 A1 | 2/2007 | Baker |
| 2007/0116723 A1 | 5/2007 | Coleman |
| 2007/0148194 A1 | 6/2007 | Amiji et al. |
| 2007/0178121 A1 | 8/2007 | First et al. |
| 2008/0274195 A1 | 11/2008 | Nicolosi et al. |
| 2009/0306198 A1 | 12/2009 | Nicolosi et al. |
| 2010/0040883 A1 | 2/2010 | McCarthy et al. |
| 2010/0183726 A1 | 7/2010 | Nicolosi et al. |
| 2011/0020227 A1 | 1/2011 | Mccarthy et al. |
| 2011/0206739 A1 | 8/2011 | Nicolosi et al. |

FOREIGN PATENT DOCUMENTS

| | | |
|---|---|---|
| EP | 0572080 A1 | 12/1993 |
| EP | 0770422 | 5/1997 |
| EP | 1080720 | 3/2001 |
| EP | 1652515 | 5/2006 |
| EP | 1249232 | 10/2006 |
| JP | 2002308728 | 10/2002 |
| WO | WO 94/20072 | 9/1994 |
| WO | WO 95/22973 | 8/1995 |
| WO | WO98/51278 | 11/1998 |
| WO | WO 99/07238 | 2/1999 |
| WO | WO-0038653 A1 | 7/2000 |
| WO | WO-0110413 A2 | 2/2001 |
| WO | WO 01/070197 | 9/2001 |
| WO | WO 02/056866 A1 * | 7/2002 |
| WO | WO 02/080864 | 10/2002 |
| WO | WO-03101483 | 12/2003 |
| WO | WO-2004006954 A2 | 1/2004 |
| WO | WO-2004076634 A2 | 9/2004 |
| WO | WO-2004084839 A2 | 10/2004 |
| WO | WO-2005/020962 A1 | 3/2005 |
| WO | WO-2005020962 A1 | 3/2005 |
| WO | WO-2005027872 A2 | 3/2005 |
| WO | WO 2005/042539 | 5/2005 |
| WO | WO2005/063377 | 7/2005 |
| WO | WO2005/084361 | 9/2005 |
| WO | WO-2005/102285 A1 | 11/2005 |
| WO | WO-2006005910 A2 | 1/2006 |
| WO | WO-2006050926 | 5/2006 |
| WO | WO-2006084353 A1 | 8/2006 |
| WO | WO-2006094263 A2 | 9/2006 |
| WO | WO-2006138127 A2 | 12/2006 |
| WO | WO-2007041664 A1 | 4/2007 |
| WO | WO-2007089454 A2 | 8/2007 |
| WO | WO-2007103555 A2 | 9/2007 |

OTHER PUBLICATIONS

Choi et al., "Percutaneous Absorption", Fourth Edition, vol. 155, Bronaugh and Maibach ed., Taylor and Francis, Boca Ratonm Florida, 2005, Index and Table of contents only, 33 pages.

Hickerson et al., "SiRNA-Mediated Selective Inhibition of Mutant Keratin mRNAs Responsible for the Skin Disorder Pachyonychia Congenita", Ann. N.Y. Acad. Sci., 1082:56-61 (2006).

Kitson, "Drugs Used for Skin Diseases," Published in Dermatologic, Cosmeceutic, and Cosmetic Development Therapeutic and Novel Approaches, Ed. Walters and Roberts, pp. 11-20 (2008).

Lin et al., "Delivery of plasmid DNA expression vector for karatinocyte growth factor-1 using electroporation to improve cutaneous wound healing in a septic rat model", Wound Repair and Regeneration, 14:618-624 (2006).

Delgado-Charro et al., "Delivery of a hydrophilic solute through the skin from novel microemulsion systems," Eur. J. Pharmaceutics and Biopharmaceutics, 43(1):37-42, 1997.

Schmalfuss et al., "Modification of drug penetration into human skin using microemulsions," J. Controlled Release, 46(3):279-285, 1997.

Wu et al., "Topical Transfection Using Plasmid DNA in a Water-in-Oil Nanoemulsion," Int. J. Pharmceutics, 221(1/02):23-34, 2001.

Wu et al., "Topical Transport of Hydrophilic Compounds Using Water-in-Oil Nanoemusions," Int. J. Pharmaceutics, 220:63-75, 2001.

Supplementary European Search Report for Application No. EP06851782, dated Jul. 3, 2012.

De Campo et al., "Five-component food-grade microemulsions: structural characterization by SANS," J. Colloid and Interface Sci., 274:251-267 (2004).

* cited by examiner

Figure 3A:
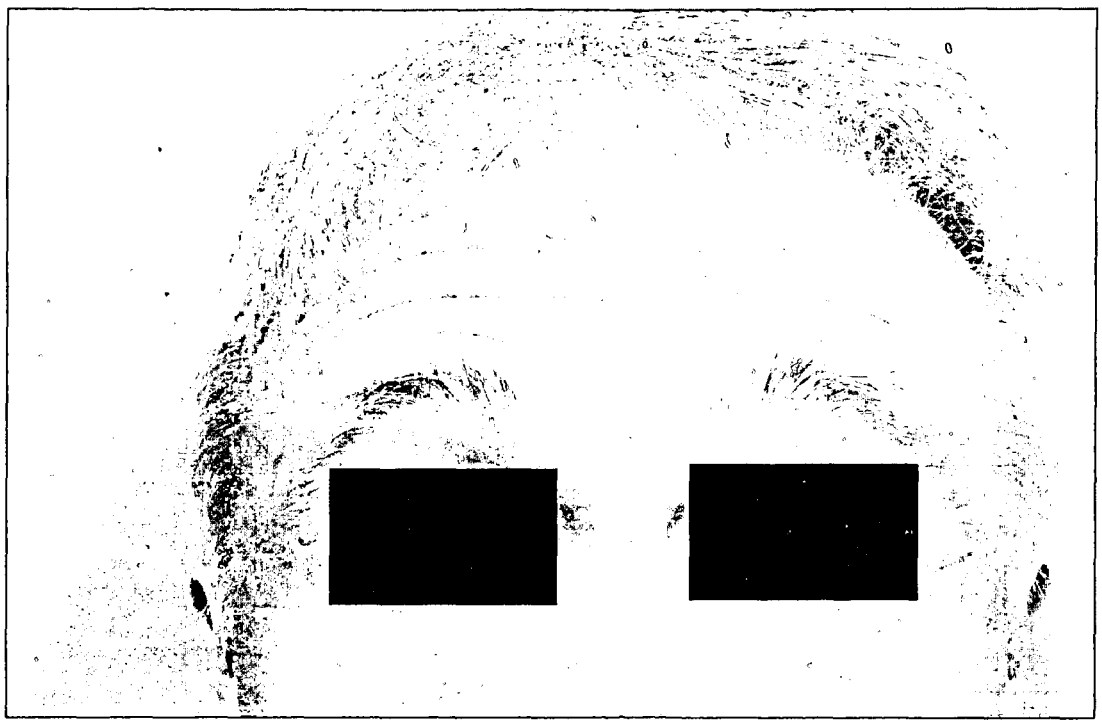
Figure 3B:
Figure 3

BOTULINUM NANOEMULSIONS

RELATED APPLICATIONS

The present application is related to and claims priority under 35 USC 119(e) to U.S. Ser. No. 60/741,139, filed Dec. 1, 2005 (the '139 application); the entire contents of the '139 application are incorporated herein by reference.

BACKGROUND

Botulinum toxin has been used in cosmetic dermatology to treat a variety of skin conditions and disorders. For example, botulinum toxin has been used to treat wrinkles (e.g., hyperkinetic facial lines), platysma bands, décolleté bands, hyperhidrosis, and certain neuromuscular disorders. Typically, botulinum toxin is delivered by injection into the site of interest (i.e., into the relevant muscle group responsible for wrinkle or band formation; into skin containing sweat glands; etc).

Unfortunately, current strategies for delivering botulinum toxin generate numerous adverse effects. For example, improper injection techniques can damage tissue and/or can deliver botulinum toxin to unintended and/or undesirable locations. In the periocular region, lid and brow ptosis are important adverse effects. Pain, hematoma, ecchymosis, and bruising can also occur.

Although techniques (e.g., cooling the skin prior to injection to reduce pain, hematoma, ecchymosis, and bruising) have been developed that can minimize certain side effects, there remains a need for the development of improved systems and/or formulations for delivering botulinum toxin.

SUMMARY OF THE INVENTION

The present invention provides nanoparticle compositions (e.g., nanoemulsions) containing botulinum toxin. Such compositions are useful, for example, in various cosmetic and medical applications. In some embodiments of the invention, botulinum nanoparticle compositions are utilized to smooth wrinkles. In some embodiments of the invention, botulinum nanoparticle compositions are utilized to treat hyperhidrosis. In some embodiments of the invention, botulinum nanoparticle compositions are utilized to treat muscle contracture and/or overactivity. Other uses of the inventive botulinum nanoparticle compositions are described herein and/or will be apparent to one of ordinary skill in the art.

In some embodiments of the present invention, botulinum nanoparticle compositions are prepared by exposure to high shear forces; in some embodiments, botulinum nanoparticle compositions are prepared by microfluidization; in some embodiments, botulinum nanoparticle compositions are prepared by high pressure homogenization.

Inventive botulinum nanoparticle compositions can be administered by any available means including, but not limited to, transdermally and by injection (e.g., intravenous, subcutaneous, or intramuscular injection). The present invention encompasses the finding that certain botulinum toxin nanoparticle compositions can be delivered transdermally without changing or altering the structure of the skin. For example, abrasive agents or agents that erode or deteriorate the superficial layer of the skin are not required to achieve transdermal delivery of botulinum toxin according to the present invention. Thus, in many embodiments, transdermal delivery of botulinum toxin is accomplished without significant irritation to the skin.

According to the present invention, transdermal delivery may be accomplished in any of a variety of formats. In some embodiments, an inventive botulinum nanoparticle composition is incorporated within a cream such that botulinum toxin is administered to a subject by application of the cream to the skin. In some embodiments, an inventive botulinum nanoparticle composition is incorporated within a transdermal patch such that botulinum toxin is administered to a subject from the patch.

In some embodiments, inventive botulinum nanoparticle compositions are emulsions containing a population of particles having maximum and minimum diameters, wherein the difference between the maximum and minimum diameters does not exceed about 600, 550, 500, 450, 400, 350, 300, 250, 200, 150, 100, 90, 80, 70, 60, 50, or fewer nm.

In some embodiments, particles (e.g., botulinum-toxin-containing particles) within inventive botulinum nanoparticle compositions have diameters that are smaller than about 600, 550, 500, 450, 400, 350, 300, 250, 200, 150, 130, 120, 115, 110, 100, 90, 80 nm, or less.

In some embodiments, particles (e.g., botulinum-toxin-containing particles) within inventive botulinum nanoparticle compositions have diameters within the range of about 10 and about 600 nanometers. In some embodiments, particles within inventive botulinum nanoparticle compositions have diameters within the range of about 10-300, 10-200, 10-150, 10-130, 10-120, 10-115, 10-110, 10-100, or 10-90 nm.

In some embodiments, particles (e.g., botulinum-toxin-containing particles) within inventive botulinum nanoparticle compositions have an average particle size that is under about 300, 250, 200, 150, 130, 120, or 115, 110, 100, or 90 nm. In some embodiments, the average particle size is within the range of about 10-300, 50-250, 60-200, 65-150, 70-130 nm. In some embodiments, the average particle size is about 80-110 nm. In some embodiments, the average particle size is about 90-100 nm.

In some embodiments, a majority of the particles (e.g., botulinum-toxin-containing particles) within inventive compositions have diameters below a specified size or within a specified range. In some embodiments, the majority is more than 50%, 60%, 70%, 75%, 80%, 85%, 90%, 95%, 96%, 97%, 98%, 99%, 99.5%, 99.6%, 99.7%, 99.8%, 99.9% or more of the particles in the composition.

In some embodiments, inventive nanoparticle compositions are substantially free of particles (e.g., botulinum-toxin-containing particles) having diameters greater than about 120 nanometers. In some embodiments, particles (e.g., botulinum-toxin-containing particles) within inventive botulinum nanoparticle compositions have diameters within the range of about 30 and about 115 nanometers. In some embodiments, most of the particles (e.g., botulinum-toxin-containing particles) within the composition have diameters within this range; in some embodiments, such compositions are substantially free of particles (e.g., botulinum-toxin-containing particles) having diameters larger than about 115 nanometers. In some embodiments, particles (e.g., botulinum-toxin-containing particles) within inventive botulinum nanoparticle compositions have diameters within the range of about 30 to about 70 nanometers. In some embodiments, most of the particles (e.g., botulinum-toxin-containing particles) within such compositions have diameters within this range; in some embodiments the compositions are substantially free of particles with diameters larger than about 70 nanometers.

In some embodiments, inventive nanoparticle compositions have at least two distinct populations of particles. For example, in some such embodiments, a majority of the particles in inventive nanoparticle compositions have diameters within the range of about 30-70 nm, while a second population of particles has diameters within the range of 70-120 nm. In some such embodiments, the composition is not contaminated with particles greater than 120 nm in diameter.

In some embodiments, botulinum toxin is present partially or entirely within nanoparticles in inventive botulinum nanoparticle compositions; in some embodiments, botulinum toxin is adsorbed on the surface of nanoparticles in inventive botulinum compositions; in some embodiments, botulinum toxin is associated with the interface between the nanoparticles and the dispersion medium. In some embodiments, botulinum toxin is found in two or more of these locations within the nanoparticle composition.

In some embodiments of the invention, the botulinum toxin is selected from the group consisting of type A, type B, type $C_1$, type $C_2$, type D, type F, and type G. In some embodiments, the botulinum toxin is present as an isolated protein; in some embodiments, the botulinum toxin is present as part of a protein complex.

This application refers to various patent publications, all of which are incorporated herein by reference.

DEFINITIONS

Abrasion: The term "abrasion," as used herein refers to any means of altering, disrupting, removing, or destroying the top layer of the skin. In some embodiments, abrasion refers to a mechanical means of altering, disrupting, removing, or destroying the top layer of the skin. In some embodiments, abrasion refers to a chemical means of altering, disrupting, removing, or destroying the top layer of skin. To give but a few examples, agents such as exfoliants, fine particles (e.g. magnesium or aluminum particles), acids (e.g. alpha-hydroxy acids or beta-hydroxy acids), alcohols, may cause abrasion. In general, permeation enhancers such as those described, for example, by Donovan (e.g. US Publications 2004/009180 and 2005/175636, and PCT Publication WO 04/06954), and Graham (e.g. U.S. Pat. No. 6,939,852 and US Publication 2006/093624), etc., are expected to cause abrasion. Of course, those of ordinary skill in the art will appreciate that a particular agent may cause abrasion when present at one concentration, or in association with one or more other agents, but may not cause abrasion under different circumstances. Thus, whether or not a particular material is an "abrasive agent" depends on context. Abrasion can readily be assessed by those of ordinary skill in the art, for example by observation of redness or irritation of the skin and/or histologic examination of skin showing alteration, disruption, removal, or erosion of the stratum corneum.

Administration: The term "administration," as used herein to refer to the delivery of an inventive nanoparticle composition to a subject, is not limited to any particular route but rather refers to any route accepted as appropriate by the medical community. For example, the present invention contemplates routes of delivering or administering that include, but are not limited to, transdermal, intramuscular, or subcutaneous. In certain embodiments of the invention, administration is transdermal.

Biologically active agent: As used herein, the phrase "biologically active agent" refers to any substance that has activity in a biological system and/or organism. For instance, a substance that, when administered to an organism, has a biological effect on that organism, is considered to be biologically active. In particular embodiments, where a protein or polypeptide is biologically active, a portion of that protein or polypeptide that shares at least one biological activity of the protein or polypeptide is typically referred to as a "biologically active" portion. Botulinum toxin is a biologically active agent in accordance with the present invention.

Botulinum nanoparticle composition: The term "botulinum nanoparticle composition," as used herein, refers to any nanoparticle composition in which at least one nanoparticle includes botulinum toxin. The botulinum toxin may be present within the nanoparticle, on the nanoparticle surface and/or within a micellar membrane defining the nanoparticle.

Botulinum toxin: The term "botulinum toxin," as used herein, refers to any neurotoxin produced by *Clostridium botulinum*. Except as otherwise indicated, the term encompasses fragments or portions (e.g., the light chain and/or the heavy chain) of such neurotoxin that retain appropriate activity (e.g., muscle relaxant activity). The phrase "botulinum toxin," as used herein, encompasses the botulinum toxin serotypes A, B, C, D, E, F, and G. Botulinum toxin, as used herein, also encompasses both a botulinum toxin complex (i.e., for example, the 300, 600, and 900 kD complexes) as well as the purified (i.e., for example, isolated) botulinum toxin (i.e., for example, about 150 kD). "Purified botulinum toxin" is defined as a botulinum toxin that is isolated, or substantially isolated, from other proteins, including protein that for a botulinum toxin complex. A purified toxin may be greater than 95% pure, and preferably is greater than 99% pure. Those of ordinary skill in the art will appreciate that the present invention is not limited to any particular source of botulinum toxin. For example, botulinum toxin for use in accordance with the present invention may be isolated from *Clostridium botulinum*, may be chemically synthesized, may be produced recombinantly (i.e., in a host cell or organism other than *Clostridium botulinum*), etc.

Cosmeceutical: The term "cosmeceutical," as used herein, refers to any agent (e.g., for example, benzoyl peroxide or retinol) that possesses both cosmetic and pharmaceutical properties. A cosmeceutical is generally useful for external applications to improve the complexion or overall physical appearance. Cosmeceuticals may be applied as compositions including, but not limited to, creams, oils, foams, sprays, liquids etc. To give but a few examples, carotenoids, phenolic compounds and/or water soluble antioxidants may act as cosmeceuticals.

Cosmetic formulation: The term "cosmetic formulation" is used herein to refer to a topically applied composition that contains one or more agents having cosmetic properties. To give but a few examples, a cosmetic formulation may be a skin softener, nutrition lotion type emulsion, cleansing lotion, cleansing cream, skin milk, emollient lotion, massage cream, emollient cream, make-up base, lipstick, facial pack or facial gel, cleaner formulation such as shampoos, rinses, body cleanser, hair-tonics, or soaps, and/or a dermatological composition such as a lotion, ointment, gel, cream, patch and/or spray.

Cream: The term "cream" refers to a spreadable composition, typically formulated for application to the skin. Creams typically contain an oil and/or fatty acid based-matrix. Creams formulated according to the present invention may contain nanoparticles and may be capable of substantially complete penetration (e.g., of such nanoparticles) through the skin upon topical administration. Such a cream could also act as a carrier for incorporated materials (e.g., for example, for a botulinum toxin).

Dispersion medium: The term "dispersion medium" as used herein, refers to a liquid medium in which particles (e.g., nanoparticles) are dispersed. In general, a dispersion is formed when at least two immiscible materials are combined. An "oil-in-water" dispersion is one in which oily particles are dispersed within an aqueous dispersion medium. A "waterin-oil" dispersion is one in which aqueous particles are dispersed within an oily dispersion medium. Those of ordinary skill in the art will appreciate that a dispersion can be formed from any two immiscible media and is not limited strictly to combinations of aqueous and oily media. The term "dispersion medium" therefore applies broadly to any dispersion medium notwithstanding that it is common to refer to "aqueous" and "oily" categories.

Encapsulated: The term "encapsulated" (also "encapsulate" or "encapsulating") is used herein to mean that the encapsulated entity is completely surrounded by another material. To give but one example, a biologically active agent (e.g., botulinum toxin) may be encapsulated within a nanoparticle in an inventive emulsion. Such encapsulation may be achieved, for example, during formation of a nanoparticle composition (e.g., a nanoemulsion), for example during microfluidization.

In conjunction with: As used herein, the phrase delivered "in conjunction with" refers to the co-delivery of two or more things. In particular, according to the present invention, the phrase is used herein in reference to delivery of a biologically active agent with inventive nanoparticles and/or nanoparticle compositions. A substance or agent is delivered in conjunction with nanoparticles when the substance or agent is combined with nanoparticles and/or nanoparticle compositions; is encapsulated or completely surrounded by nanoparticles; is associated with a nanoparticle interface; and/or is adsorbed to the outer surface of a nanoparticle. A substance or agent to be delivered in conjunction with nanoparticles and/or nanoparticle compositions may or may not be covalently linked to the nanoparticles and/or nanoparticle compositions. A substance or agent to be delivered in conjunction with nanoparticles and/or nanoparticle compositions may or may not be attached to the nanoparticles and/or nanoparticle compositions by adsorption forces. In many embodiments of the present invention, the biologically active agent delivered in conjunction with a nanoparticle or nanoparticle composition is botulinum toxin.

Microfluidized: The term "microfluidized" is generally used herein to describe compositions that have been exposed to high shear force. In some embodiments of the invention, the compositions have been processed by an instrument or a device known as a "Microfluidizer®." However, in its broadest sense, the term encompasses any composition that has been exposed to high shear force by any means. For example, high shear force may be administered by cavitation or by high pressure homogenization. Alternatively or additionally, high shear force may be administered by exposure to high pressure, for example about 15,000 psi. In some embodiments, such high pressure is within the range of about 18,000 to about 26,000 psi; in some embodiments, it is within the range of about 20,000 to 25,000 psi. As indicated, high shear force may be administered by passage through an instrument such as, for example, a Microfluidizer® Processor (Microfluidics Corporation/MFIC Corporation) or other like device. Microfluidizer® Processors provide high pressure and a resultant high shear rate by accelerating the product through microchannels to a high velocity for size reduction to the nanoscale range. The fluid is split in two and is pushed through microchannels with typical dimensions in the order of 75 microns at high velocities (in the range of 50-300 mls). As the fluid exits the microchannels it forms jets which collide with jets from opposing microchannels. In the channels the fluid experiences high shear (up to $10^7$ l/s) which is orders of magnitude higher than that of conventional technologies. Jet collisions result in mixing in submicron level. Therefore, high shear and impact are responsible for particle size reduction and mixing of multiphase fluids in the Microfluidizer® technology. In some embodiments of the present invention, a sample is "microfluidized" through exposure to high shear forces for a period of time less than about 10 minutes. In some embodiments, the period of time is less than about 9, 8, 7, 6, 5, 4, 3, 2, or 1 minute(s). In some embodiments, the period of time is within the range of about 1-2 minutes or less; in some embodiments, the period of time is about 30 seconds. In some embodiments of the invention, a sample is "microfluidized" through a single exposure to high shear forces; such embodiments are referred to herein as "single pass" microfluidization.

Nanoemulsion: An emulsion is traditionally defined in the art "as a system . . . consisting of a liquid dispersed with or without an emulsifier in an immiscible liquid usually in droplets of larger than colloidal size" *Medline Plus Online Medical Dictionary, Merriam Webster* (2005). The term "nanoemulsion," as used herein, refers to an emulsion in which at least some of the droplets (or particles) have diameters in the nanometer size range. As will be understood by those of ordinary skill in the art, a nanoemulsion is characterized by droplets or particles one thousand fold smaller than microemulsion droplets or particles.

Nanoparticle: As used herein, the term "nanoparticle" refers to any particle having a diameter of less than 1000 nanometers (nm). In some embodiments, a nanoparticle has a diameter of less than 300 nm, as defined by the National Science Foundation. In some embodiments, a nanoparticle has a diameter of less than 100 nm as defined by the National Institutes of Health. Those of ordinary skill in the art will appreciate that, the term "nanoparticle" as used herein describes the dispersed phase in a dispersion or emulsion.

Nanoparticle composition: As used herein, the term "nanoparticle composition" refers to any composition that includes at least one nanoparticle. In some embodiments, a nanoparticle composition is a uniform collection of nanoparticles. Nanoparticle compositions described herein are typically emulsions or dispersions. In some embodiments, a nanoparticle composition is stable. In some embodiments, a nanoparticle composition includes one or more biologically active agents to be delivered in conjunction with the nanoparticles. In some embodiments, the nanoparticle composition is a nanoemulsion. It will be appreciated by those of ordinary skill in the art that a nanoparticle composition may be prepared according to any available means including, for example, chemical or mechanical means. In some embodiments of the present invention, a nanoparticle composition is prepared by subjecting a sample to microfluidization. In some embodiments of the invention, a nanoparticle composition is prepared without use of toxic solvents and/or is substantially free of toxic solvents.

Not contaminated with: The phrase "not contaminated with," when used herein to refer to a nanoparticle composition, is synonymous with "substantially free of" and describes a nanoparticle composition containing no more than about 50% of the recited material. For example, if a nanoparticle composition is said to be "substantially free of" particles whose diameter is outside of a stated range, then no more than about 50% of the particles in that composition have diameters outside of the range. In some embodiments, no more than 25% of the particles are outside of the range. In some embodiments, no more than 20%, 19%, 18%, 17%, 16%, 15%, 14%, 13%, 12%, 10%, 9%, 8%, 7%, 6%, 5%, 4%, 3%, 2%, 1%, 0.5% or less of the particles have diameters outside of the stated range.

Pharmaceutically acceptable: The term "pharmaceutically acceptable" as used herein, refers to agents that, within the scope of sound medical judgment, are suitable for use in contact with the tissues of human beings and animals without excessive toxicity, irritation, allergic response, or other problem or complication, commensurate with a reasonable benefit/risk ratio.

Premix: The term "premix" as used herein, refers to any combination of components that is subsequently used to generate a nanoparticle composition or according to the present invention. For example, a premix is any collection of ingredients that, when subjected to high shear force, generates nanoparticles according to the present invention. In some embodiments, a premix is a collection of ingredients that, when subjected to high shear force, generates a nanoparticle composition such as a uniform nanoparticle composition. A premix often contains a liquid dispersion medium and other components sufficient to generate nanoparticles within the dispersion medium. According to the present invention, botulinum toxin may also be included in the premix. The premix may also contain one or more surfactants and/or other agents. In some embodiments, the premix constitutes a solution. In some particular embodiments in which the premix includes botulinum toxin and/or another biologically active agent, the botulinum toxin (and/or other biologically active agent) is in solution before high shear force is applied to the premix.

Refractory: The term "refractory" as used herein, refers to any subject that does not respond with an expected clinical efficacy following the delivery of a biologically active agent or pharmaceutical composition as normally observed by practicing medical personnel.

Self-administration: The term "self-administration," as used herein, refers to the situation where a subject has the ability to administer a composition to him or herself without requiring medical supervision. In some embodiments of the invention, self-administration may be performed outside of a clinical setting. To give but one example, in some embodiments of the invention, a facial cosmetic cream may be administered by a subject in one's own home.

Small Molecule: In general, a "small molecule" is understood in the art to be an organic molecule that is less than about 5 kilodaltons (Kd) in size. In some embodiments, the small molecule is less than about 3 Kd, 2 Kd, or 1 Kd. In some embodiments, the small molecule is less than about 800 daltons (D), 600 D, 500 D, 400 D, 300 D, 200 D, or 100 D. In some embodiments, small molecules are non-polymeric. In some embodiments, small molecules are not proteins, peptides, or amino acids. In some embodiments, small molecules are not nucleic acids or nucleotides. In some embodiments, small molecules are not saccharides or polysaccharides.

Stable: The term "stable," when applied to nanoparticle compositions herein, means that the compositions maintain one or more aspects of their physical structure (e.g., size range and/or distribution of particles) over a period of time. In some embodiments of the invention, a stable nanoparticle composition is one for which the average particle size, the maximum particle size, the range of particle sizes, and/or the distribution of particle sizes (i.e., the percentage of particles above a designated size and/or outside a designated range of sizes) is maintained for a period of time. In some embodiments, the period of time is at least about one hour; in some embodiments the period of time is about 5 hours, 10 hours, one (1) day, one (1) week, two (2) weeks, one (1) month, two (2) months, three (3) months, four (4) months, five (5) months, six (6) months, eight (8) months, ten (10) months, twelve (12) months, twenty-four (24) months, or longer. In some embodiments, the period of time is within the range of about one (1) day to twenty-four (24) months, two (2) weeks to twelve (12) months, two (2) months to five (5) months, etc. For example, if a population of nanoemulsion particles is subjected to prolonged storage, temperature changes, and/or pH changes and a majority of the nanoparticles in the population maintain a diameter within a stated range (i.e., for example, between approximately 10-120 nm), the nanoemulsion is stable. For some such populations, a majority is more than about 50%, 60%, 70%, 80%, 90%, 95%, 96%, 97%, 98%, 99%, 99.5%, 99.6%, 99.7%, 99.8%, 99.9% or more. In some embodiments of the invention, where a nanoparticle composition comprises botulinum toxin and/or at least one other biologically active agent, the nanoparticle composition is considered stable if the concentration of biologically active agent (e.g., botulinum toxin) is maintained in the composition over the designated period of time under a designated set of conditions.

Subject: The term "subject" as used herein, refers to any animal to which an inventive nanoparticle composition may be delivered or administered. For example, a subject may be a human, dog, cat, cow, pig, horse, mouse, rat, gerbil, hamster etc. In many embodiments of the present invention, the subject is a human.

Symptoms are reduced: According to the present invention, "symptoms are reduced" when one or more symptoms of a particular disease, disorder or condition is reduced in magnitude (e.g., intensity) or frequency. For purposes of clarity, a delay in the onset of a particular symptom is considered one form of reducing the frequency of that symptom. To give but a few examples, where the condition in question is facial wrinkles, symptoms of that condition are reduced when the depth and/or severity of one or more wrinkles in the selected area is reduced. Where the condition in question is muscle contracture, symptoms are reduced when the muscle becomes less tense and more flaccid. It is not intended that the present invention be limited only to cases where the symptoms are eliminated. The present invention specifically contemplates treatment such that one or more symptoms is/are reduced (and the condition of the subject is thereby "improved"), albeit not completely eliminated.

Therapeutically effective amount: As used herein, the term "therapeutically effective amount" means an amount that is sufficient, when administered to an individual suffering from or susceptible to a disease, disorder, and/or condition, to treat the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response when administered or delivered to a significant number of subjects in need of such treatment. It is specifically understood that particular subjects may, in fact, be "refractory" to a "therapeutically effective amount." To give but one example, a refractory subject may have a low bioavailability such that clinical efficacy is not obtainable. In some embodiments, reference to a therapeutically effective amount may be a reference to an amount as measured in one or more specific tissues.

Toxic solvent: As used herein, the term "toxic solvent" refers to any substance that may alter, disrupt, remove, or destroy an animal's tissue. As would be understood by one of ordinary skill in the art, an animal's tissue can include living cells, dead cells, extracellular matrix, cellular junctions, biological molecules, etc. To give but a few examples, toxic solvents include dimethyl sulfoxide, dimethyl acetimide, dimethyl foramide, chloroform, tetramethyl foramide, acetone, acetates, and alkanes.

Treatment: As used herein, the term "treatment" (also "treat" or "treating") refers to any administration of a biologically active agent that partially or completely alleviates, ameliorates, relives, inhibits, delays onset of, reduces severity of and/or reduces incidence of one or more symptoms or features of a particular disease, disorder, and/or condition (e.g., facial wrinkles). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

Uniform: The term "uniform," when used herein in reference to a nanoparticle composition, refers to a nanoparticle composition in which the individual nanoparticles have a specified range of particle diameter sizes. For example, in some embodiments, a uniform nanoparticle composition is one in which the difference between the minimum diameter and maximum diameter does not exceed approximately 600, 550, 500, 450, 400, 350, 300, 250, 200, 150, 100, 90, 80, 70, 60, 50, or fewer nm. In some embodiments, particles (e.g., botulinum-toxin-containing particles) within inventive uniform botulinum nanoparticle compositions have diameters that are smaller than about 600, 550, 500, 450, 400, 350, 300, 250, 200, 150, 130, 120, 115, 110, 100, 90, 80 nm, or less. In some embodiments, particles (e.g., botulinum-toxin-containing particles) within inventive uniform botulinum nanoparticle compositions have diameters within the range of about 10 and about 600 nanometers. In some embodiments, particles within inventive uniform botulinum nanoparticle compositions have diameters within the range of about 10-300, 10-200, 10-150, 10-130, 10-120, 10-115, 10-110, 10-100, or 10-90 nm. In some embodiments, particles (e.g., botulinum-toxin-containing particles) within inventive botulinum nanoparticle compositions have an average particle size that is under about 300, 250, 200, 150, 130, 120, or 115, 110, 100, or 90 nm. In some embodiments, the average particle size is within the range of about 10-300, 50-250, 60-200, 65-150, 70-130 nm. In some embodiments, the average particle size is about 80-110 nm. In some embodiments, the average particle size is about 90-100 nm. In some embodiments, a majority of the particles (e.g., botulinum-toxin-containing particles) within inventive uniform nanoparticle compositions have diameters below a specified size or within a specified range. In some embodiments, the majority is more than 50%, 60%, 70%, 75%, 80%, 85%, 90%, 95%, 96%, 97%, 98%, 99%, 99.5%, 99.6%, 99.7%, 99.8%, 99.9% or more of the particles in the composition. In some embodiments of the invention, a uniform nanoparticle composition is achieved by microfluidization of a sample.

BRIEF DESCRIPTION OF THE DRAWING

FIG. 3 shows a patient attempting maximal brow elevation prior to (Panel A) and two weeks after (Panel B) topical administration of an inventive composition comprising a botulinum nanoparticle composition.

DESCRIPTION OF CERTAIN PREFERRED EMBODIMENTS

Figure 1:
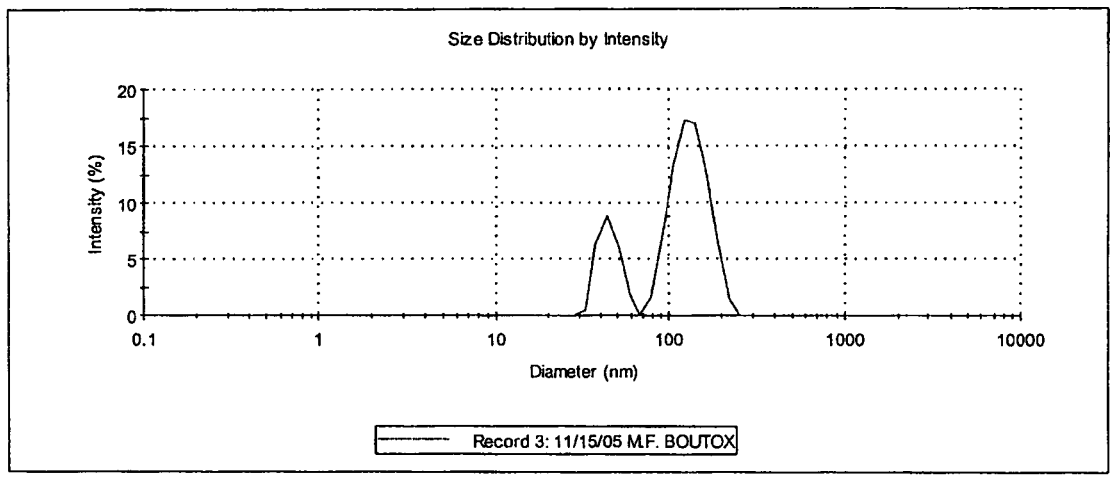
FIG. 1 shows one embodiment of a particle diameter distribution of a microfluidized botulinum toxin nanoemulsion.

The present invention relates to botulinum toxin nanoemulsion compositions useful for cosmetic and medical treatments. Among other things, the present invention provides systems for producing nanoparticle compositions that comprise botulinum toxin, and further provides methods of using such compositions in various contexts. In one embodiment, a medical treatment relieves muscular contracture and/or overactivity; in another embodiment, a medical treatment relieves hyperhidrosis. In one embodiment, a cosmetic treatment smoothes skin wrinkles. In one embodiment, a botulinum toxin nanoemulsion is prepared by microfluidization. Administration of botulinum toxin nanoemulsions may be performed by methods including but not limited to intramuscular injection or transdermal topical application.

Botulinum Toxin Biology

Botulinum toxin (BTX) BTX is produced in nature by the anaerobic, gram positive bacterium *Clostridium botulinum* and is a potent polypeptide neurotoxin. Most notably, BTX causes a neuroparalytic illness in humans and animals referred to as botulism. BTX can apparently pass untenanted through the lining of the gut and attack peripheral motor neurons. Symptoms of botulinum toxin intoxication can progress from difficulty walking, swallowing, and speaking to paralysis of the respiratory muscles, and death.

BTX-A is the most lethal natural biological agent known to man. The $LD_{50}$ in female Swiss Webster mice (18-20 g) for commercially available BTX-A is about 50 picograms; this amount is defined as 1 Unit of BTX-A. On a molar basis, BTX-A is about 1.8 billion times more lethal than diphtheria, about 600 million times more lethal than sodium cyanide, about 30 million times more lethal than cobra toxin and about 12 million times more lethal than cholera (Singh, et al., ed., "Critical Aspects of Bacterial Protein Toxins" *Natural Toxins II*, pp. 63-84, Plenum Press, New York, 1996).

The different serotypes of botulinum toxin vary in the animal species that they affect and in the severity and duration of the paralysis they evoke. For example, it has been determined that BTX-A is 500 times more potent than is BTX-B, as measured by the rate of paralysis produced in the rat. Additionally, BTX-B has been determined to be non-toxic in primates at a dose of 480 U/kg, which is about 12 times the primate $LD_{50}$ for BTX-A. Furthermore, it is known that botulinum toxin type B has, upon intramuscular injection, a shorter duration of activity and is also less potent than BTX-A at the same dose level.

Botulinum toxin apparently binds with high affinity to cholinergic motor neurons, is translocated into the neuron and blocks the release of acetylcholine.

Botulinum toxins have been used in clinical settings for the treatment of certain neuromuscular disorders. In particular, BTX-A has been approved by the U.S. Food and Drug Administration for the treatment of blepharospasm, strabismus, and hemifacial spasm. Non-type A botulinum toxin serotypes apparently have a lower potency and/or a shorter duration of activity as compared to BTX-A. Clinical effects of peripheral intramuscular BTX-A are usually seen within one week of injection. The typical duration of symptomatic relief from a single intramuscular injection of BTX-A averages about three months.

Although all the botulinum toxins serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kilodalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes. Significantly, it is known that the cytosol of pancreatic islet B cells contains at least SNAP-25 (Biochem J 1; 339 (pt 1): 159-65 (April 1999)), and synaptobrevin (Mov Disord 1995 May; 10(3): 376).

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the BTX-A complex can be produced by Clostridial bacterium as 900 kD, 500 kD and 360 kD forms. Botulinum toxin types B and $C_1$ are apparently produced as only a 500 kD complex. Botulinum toxin type D is produced as both 300 kD and 500 kD complexes. Finally, botulinum toxin types E and F are produced as only approximately 30010 complexes.

The BTX complexes (i.e., those compositions having molecular weights greater than about 150 kD) are believed to contain a non-toxin hemagglutinin protein and a non-toxin and non-toxic non-hemagglutinin protein. These two non-toxin proteins (which along with the botulinum toxin molecule comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex.

Either BTX proteins or BTX complexes may be utilized in accordance with the present invention. Indeed, it will be appreciated by those of ordinary skill in the art that any portion or fragment of a BTX protein or complex that retains the appropriate activity may be utilized as described herein.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine, CGRP and glutamate.

As noted above, the source of botulinum toxin is not critical to the present invention. For purposes of completeness, however, we note that a variety of sources, including commercial sources, for certain botulinum toxin preparations are readily available.

For example, BTX or BTX complex can be obtained by establishing and growing cultures of Clostridium botulinum in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the BTX-A serotype typically only cleave a portion of the toxin produced. The exact proportion of nicked to unnicked molecules can depend on the length of incubation and the temperature of the culture. Therefore, a certain percentage of any preparation of, for example, the BTX-A toxin is likely to be inactive. The presence of inactive botulinum toxin molecules in a clinical preparation will contribute to the overall protein load of the preparation, which has been linked in some commercially available botulinum toxin preparations to increased antigenicity, without contributing to its clinical efficacy.

High quality crystalline botulinum toxin type A can be produced from the Hall A strain of Clostridium botulinum with characteristics of $\geq 3\times 10^7$ U/mg, an $A_{260}/A_{278}$ of less than 0.60 and a distinct pattern of banding on gel electrophoresis. The known Schantz process can be used to obtain crystalline botulinum toxin including type A (Shantz et al., 1992, Microbiol. Rev., 56:80).

Generally, the botulinum toxin complex can be isolated and purified from an anaerobic fermentation by cultivating Clostridium botulinum (e.g., type A) in a suitable medium. The known process can be used, upon separation out of the non-toxin proteins, to obtain pure botulinum toxins, such as for example: purified botulinum toxin type A with an approximately 150 kD molecular weight with a specific potency of $1\text{-}2\times 10^8$ LD$_{50}$ U/mg or greater; purified botulinum toxin type B with an approximately 156 kD molecular weight with a specific potency of $1\text{-}2\times 10^8$ LD$_{50}$ U/mg or greater, and; purified botulinum toxin type F with an approximately 155 kD molecular weight with a specific potency of $1\text{-}2\times 10^7$ LD$_{50}$ U/mg or greater.

Alternatively or additionally, already prepared and purified botulinum toxins and toxin complexes can be obtained from, for example, List Biological Laboratories, Inc., Campbell, Calif.; the Centre for Applied Microbiology and Research, Porton Down, U.K.; Wako (Osaka, Japan) as well as from Sigma Chemicals of St Louis, Mo.

Pure botulinum toxin, when administered as a free solution, is so labile that it is generally not used to prepare a pharmaceutical composition. Furthermore, the botulinum toxin complexes, such the toxin type A complex can also be susceptible to denaturation due to surface denaturation, heat, and alkaline conditions. In some cases, inactivated toxin forms toxoid proteins which may be immunogenic. Resulting antibodies can render a patient refractory to toxin injection.

In some embodiments, the present invention provides botulinum toxin nanoparticle compositions (e.g., nanoemulsions) in which the botulinum toxin has improved stability when compared to currently administered free solutions. That is, in some embodiments, botulinum toxin present in an inventive nanoparticle composition is protected, at least in part, from at least one adverse condition such as heat, alkaline conditions, acidic conditions, degradative enzymes, host organism antibodies, etc. Alternatively or additionally, botulinum toxin present in inventive nanoparticle compositions may show less surface denaturation than an otherwise comparable preparation of botulinum toxin in free solution. To give but one specific example, 50 picograms a botulinum toxin within a microfluidized nanoemulsion according to the present invention will be protected from certain adverse conditions, etc that may result in surface denaturation.

Indeed, one aspect of the present invention encompasses the recognition that botulinum toxin may be stabilized by incorporation into a nanoparticle composition. Those of ordinary skill in the art will readily appreciate that a nanoparticle composition according to this aspect of the present invention may be prepared by any available means.

The present invention further provides botulinum toxin nanoparticle compositions (e.g., nanoemulsions) in which the botulinum toxin has improved ability to permeate skin when compared to currently administered free solutions. For example, botulinum toxin incorporated within a microfluidized nanoemulsion according to the present invention has improved membrane permeability properties when compared with such free solutions. In one embodiment, the minimal time between administration and intracellular accumulation results in a method of administration having improved efficacy and decreased side effects.

Moreover, as demonstrated herein, the present invention provides botulinum toxin nanoparticle compositions from which botulinum toxin can cross the skin without requiring alteration or disruption of skin structures. For example, commercially available technologies for transdermal administration of biologically active agents traditionally require chemical, physical, electrical or other disruption of at least the outer layer of skin. Such disruption can cause irritation, undesirable medical side-effects, and/or unwanted aesthetic outcomes. The present invention provides botulinum toxin nanoparticle compositions that, when administered to skin, do not significantly or noticeably irritate the skin and/or erode the stratum corneum, and yet allow botulinum toxin to permeate the skin to have its biological effects.

As with proteins generally, the biological activities of the botulinum toxins (which are intracellular peptidases) can be affected by changes in three dimensional conformation. Thus, botulinum toxin type A can be detoxified by heat, various chemicals, surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, solution preparations of the toxin must be formulated with a stabilizing agent, such as albumin.

As noted above, the present invention provides stabilized preparations of botulinum toxin. Notwithstanding the additional stability that may be imparted by the inventive formulation itself, in some embodiments of the invention, use of additional stabilizers is contemplated. For example, in some embodiments, at least one additional protein is used together with the botulinum toxin. In some embodiments, this additional protein comprises albumin. In some embodiments, this additional protein comprises one or more of the proteins naturally found in a botulinum toxin complex. Indeed, in some embodiments of the invention, a complete botulinum toxin complex is employed. In some such embodiments, albumin is also utilized. Thus, in some embodiments, the present invention provides a botulinum microfluidized nanoemulsion comprising albumin.

In some embodiments of the present invention, the botulinum toxin utilized is BOTOX®. BOTOX® consists of a purified botulinum toxin type A complex, albumin and sodium chloride packaged in sterile, vacuum-dried form.

The botulinum toxin type A present in BOTOX® is made from a culture of the Hall strain of *Clostridium botulinum* grown in a medium containing N-Z amine and yeast extract. The botulinum toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. BOTOX® can be reconstituted with sterile, non-preserved saline prior to intramuscular injection. Each vial of BOTOX® contains about 100 units (U) of *Clostridium botulinum* toxin type A purified neurotoxin complex, 0.5 milligrams of human serum albumin, and 0.9 milligrams of sodium chloride in a sterile, vacuum-dried form without a preservative.

Currently, BOTOX® is usually reconstituted with 0.9% sodium chloride for administration by injection. Since BOTOX® can be denatured by bubbling or similar violent agitation, the diluent is gently injected into the vial. BOTOX®, as a free solution, is recommended to be administered within four hours after reconstitution. Further, between reconstitution and injection, it is further recommended that reconstituted BOTOX® be stored in a refrigerator (i.e., for example, between 2° to 8° C.). Reconstituted BOTOX® is clear, colorless and free of particulate matter.

It has been reported that BOTOX® has been used in clinical settings as follows:
(1) about 75-125 units of BOTOX® per intramuscular injection (multiple muscles) to treat cervical dystonia;
(2) 5-10 units of BOTOX® per intramuscular injection to treat glabellar lines (brow furrows) (5 units injected intramuscularly into the procerus muscle and 10 units injected intramuscularly into each corrugator supercilii muscle);
(3) about 30-80 units of BOTOX® to treat constipation by intrasphincter injection of the puborectalis muscle;
(4) about 1-5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.
(5) to treat strabismus, extraocular muscles have be in injected intramuscularly with between about 1-5 units of BOTOX®, the amount injected varying based upon both the size of the muscle to be injected and the extent of muscle paralysis desired (i.e. amount of diopter correction desired).
(6) to treat upper limb spasticity following stroke by intramuscular injections of BOTOX® into five different upper limb flexor muscles, as follows:
(a) flexor digitorum profundus: 7.5 U to 30 U
(b) flexor digitorum sublimus: 7.5 U to 30 U
(c) flexor carpi ulnaris: 10 U to 40 U
(d) flexor carpi radialis: 15 U to 60 U
(e) biceps brachii: 50 U to 200 U
Each of the five indicated muscles has been injected at the same treatment session, so that the patient receives from 90 U to 360 U of upper limb flexor muscle BOTOX® by intramuscular injection at each treatment session. (7) to treat migraine, pericranial injected (injected symmetrically into glabellar, frontalis and temporalis muscles) injection of 25 U of BOTOX®has showed significant benefit as a prophylactic treatment of migraine compared to vehicle as measured by decreased measures of migraine frequency, maximal severity, associated vomiting and acute medication use over the three month period following the 25 U injection.

The present invention demonstrates (see, for example, Examples 4 and 5) that an inventive botulinum nanoparticle composition containing BOTOX®, when incorporated into a cream that is applied to the skin for transdermal delivery of the toxin, achieves biological results (i.e., reduction of wrinkles) comparable to those historically observed with injection of a botulinum toxin solution containing approximately the same about of BOTOX®.

The positive clinical responses of botulinum toxin type A has led to interest in other botulinum toxin serotypes. A study of two commercially available botulinum type A preparations (BOTOX® and DYSPORT®) and preparations of botulinum toxins type B and F (both obtained from Wako Chemicals, Japan) has been carried out to determine local muscle weakening efficacy, safety and antigenic potential. Botulinum toxin preparations were injected into the head of the right gastrocnemius muscle (0.5 to 200.0 units/kg) and muscle weakness was assessed using the mouse digit abduction scoring assay (DAS). $ED_{50}$ values were calculated from dose response curves.

Additional mice were given intramuscular injections to determine $LD_{50}$ doses. The therapeutic index was calculated as $LD_{50}/ED_{50}$. Separate groups of mice received hind limb injections of BOTOX® (5.0 to 10.0 units/kg) or botulinum toxin type B (50.0 to 400.0 units/kg), and were tested for muscle weakness and increased water consumption, the later being a putative model for dry mouth. Antigenic potential was assessed by monthly intramuscular injections in rabbits (1.5 or 6.5 ng/kg for botulinum toxin type B or 0.15 ng/kg for BOTOX®). Peak muscle weakness and duration were dose related for all serotypes.

DAS $ED_{50}$ values (units/kg) were as follows: BOTOX®: 6.7, DYSPORT®: 24.7, botulinum toxin type B: 27.0 to 244.0, botulinum toxin type F: 4.3. BOTOX® had a longer duration of action than botulinum toxin type B or botulinum toxin type F. Therapeutic index values were as follows: BOTOX®: 10.5, DYSPORT®: 6.3, botulinum toxin type B: 3.2. Water consumption was greater in mice injected with botulinum toxin type B than with BOTOX®, although botulinum toxin type B was less effective at weakening muscles. After four months of injections 2 of 4 (where treated with 1.5 ng/kg) and 4 of 4 (where treated with 6.5 ng/kg) rabbits developed antibodies against botulinum toxin type B. In a separate study, 0 of 9 BOTOX® treated rabbits demonstrated antibodies against botulinum toxin type A. DAS results indicate relative peak potencies of botulinum toxin type A being equal to botulinum toxin type F, and botulinum toxin type F being greater than botulinum toxin type B. With regard to duration of effect, botulinum toxin type A was greater than botulinum toxin type B, and botulinum toxin type B duration of effect was greater than botulinum toxin type F. As shown by the therapeutic index values; the two commercial preparations of botulinum toxin type A (BOTOX® and DYSPORT®) are different. The increased water consumption behavior observed following hind limb injection of botulinum toxin type B indicates that clinically significant amounts of this serotype entered the murine systemic circulation. The results also indicate that in order to achieve efficacy comparable to botulinum toxin type A, it is necessary to increase doses of the other serotypes examined. Increased dosage, however, can compromise safety. Furthermore, in rabbits, type B was more antigenic than was BOTOX®, possibly because of the higher protein load injected to achieve an effective dose of botulinum toxin type B. *Eur J Neurol* 6(Suppl 4):S3-S10 (1999).

As indicated herein, the present invention contemplates use of botulinum toxin of any serotype. Those of ordinary skill in the art will readily be able to assess the appropriateness of a particular serotype for a particular use and, according to the teachings herein, will be able to prepare nanoparticle compositions containing such botulinum toxin. Thus, the present invention provides nanoparticle compositions containing botulinum toxin of any serotype, including compositions containing only botulinum toxin proteins and compositions containing one or other proteins. In some embodiments, such other proteins comprise or consist of albumin; in some embodiments, botulinum toxin complexes are employed.

Commercially available sources of botulinum toxin that may be utilized in accordance with the present invention include, but are not limited to, BOTOX®, DYSPORT® (*Clostridium botulinum* type A toxin hemagglutinin complex with human serum albumin and lactose; Ispen Limited, Berkshire U.K.) and/or MYOBLOC® (an injectable solution consisting of botulinum toxin type B, human serum albumin, sodium succinate, and sodium chloride, pH 5.6, Elan Pharmaceuticals, Dublin, Ireland), etc.

Nanoparticle Compositions

As described herein, the present invention provides, among other things, compositions that nanoparticle compositions including nanoparticle compositions that contain botulinum toxin.

In general, a nanoparticle composition is any composition that includes at least one nanoparticle. Botulinum nanoparticle compositions are nanoparticle compositions that contain botulinum toxin. The botulinum toxin may be encapsulated or completely surrounded by one or more nanoparticles; associated with the nanoparticle interface; and/or adsorbed to the outer surface of one or more nanoparticles. Botulinum toxin may or may not be covalently linked to the nanoparticles and/or nanoparticle compositions; botulinum toxin may or may not be attached to the nanoparticles and/or nanoparticle compositions by adsorption forces.

In some embodiments, inventive nanoparticle compositions have a uniform collection of nanoparticles. For example, in some embodiments, the difference between the minimum diameter and maximum diameter of the nanoparticles in an inventive nanoparticle composition does not exceed approximately 600, 550, 500, 450, 400, 350, 300, 250, 200, 150, 100, 90, 80, 70, 60, 50, or fewer nm.

In some embodiments, particles (e.g., botulinum-toxin-containing particles) within inventive botulinum nanoparticle compositions have diameters that are smaller than about 600, 550, 500, 450, 400, 350, 300, 250, 200, 150, 130, 120, 115, 110, 100, 90, 80 nm, or less.

In some embodiments, particles (e.g., botulinum-toxin-containing particles) within inventive botulinum nanoparticle compositions have diameters within the range of about 10 and about 600 nanometers. In some embodiments, particles within inventive botulinum nanoparticle compositions have diameters within the range of about 10-300, 10-200, 10-150, 10-130, 10-120, 10-115, 10-110, 10-100, or 10-90 nm.

In some embodiments, particles (e.g., botulinum-toxin-containing particles) within inventive botulinum nanoparticle compositions have an average particle size that is under about 300, 250, 200, 150, 130, 120, or 115, 110, 100, or 90 nm. In some embodiments, the average particle size is within the range of about 10-300, 50-250, 60-200, 65-150, 70-130 nm. In some embodiments, the average particle size is about 80-110 nm. In some embodiments, the average particle size is about 90-100 nm.

In some embodiments, a majority of the particles (e.g., botulinum-toxin-containing particles) within inventive compositions have diameters below a specified size or within a specified range. In some embodiments, the majority is more than 50%, 60%, 70%, 75%, 80%, 85%, 90%, 95%, 96%, 97%, 98%, 99%, 99.5%, 99.6%, 99.7%, 99.8%, 99.9% or more of the particles in the composition.

In some embodiments, inventive nanoparticle compositions are substantially free of particles having a diameter in excess of 120 nm. Specifically, in some embodiments, fewer than 50%, of the nanoparticles in inventive nanoparticle compositions have a diameter in excess of 120 nm. In some embodiments, fewer than 25% of the particles have a diameter in excess of 120 nm. In some embodiments, fewer than 20%, 19%, 18%, 17%, 16%, 15%, 14%, 13%, 12%, 10%, 9%, 8%, 7%, 6%, 5%, 4%, 3%, 2%, 1%, 0.5% or less of the particles have a diameter in excess of 120 nm. Furthermore, in some embodiments, the nanoparticles in inventive nanoparticle compositions have diameters within the range of 10-120 nm.

Zeta potential is a measurement of the electric potential at a shear plane. A shear plane is an imaginary surface separating a thin layer of liquid bound to a solid surface (e.g. the surface of inventive nanoparticles) and showing elastic behavior from the rest of liquid (e.g. liquid dispersion medium) showing normal viscous behavior. In some embodiments, inventive nanoparticles have a zeta potential ranging between −50 mV to +50 mV. In some embodiments, inventive nanoparticles have a zeta potential ranging between −25 mV to +25 mV. In some embodiments, inventive nanoparticles have a zeta potential ranging between −10 mV to +10 mV.

Inventive nanoparticle compositions are typically emulsions or dispersions. In some embodiments, the compositions are "oil-in-water" dispersions (i.e., dispersions in which oily particles are dispersed within an aqueous dispersion medium); in some embodiments, the compositions are "water-in-oil" dispersions (i.e., dispersions in which aqueous particles are dispersed within an oily dispersion medium).

In some embodiments, inventive nanoparticle compositions do not require toxic solvents. By contrast, many conventional strategies for inducing formation of nanoparticles in a composition utilize toxic (typically organic) solvents. In some embodiments, inventive nanoparticle compositions do not require polymers. By contrast, many conventional strategies for preparing compositions that contain nanoparticle structures require polymers.

In some embodiments, inventive nanoparticle compositions have better tissue absorption and/or better biocompatibility than other nanoparticle compositions. For example, in some embodiments, inventive nanoparticle compositions have better tissue absorption and/or better biocompatibility than nanoparticle compositions that are not uniform, that utilize one or more toxic (e.g., organic) solvents, and/or that utilize one or more polymers.

In some embodiments, inventive nanoparticle compositions (e.g., botulinum nanoparticle compositions) are stable. In some embodiments of the invention, a stable nanoparticle composition is one for which the average particle size, the maximum particle size, the range of particle sizes, and/or the distribution of particle sizes (i.e., the percentage of particles above a designated size and/or outside a designated range of sizes) is maintained for a period of time. In some embodiments, the period of time is at least about one hour; in some embodiments the period of time is about 5 hours, 10 hours, one (1) day, one (1) week, two (2) weeks, one (1) month, two (2) months, three (3) months, four (4) months, five (5) months, six (6) months, eight (8) months, ten (10) months, twelve (12) months, twenty-four (24) months, or longer. In some embodiments, the period of time is within the range of about one (1) day to twenty-four (24) months, two (2) weeks to twelve (12) months, two (2) months to five (5) months, etc. For example, if a population of nanoemulsion particles is subjected to prolonged storage, temperature changes, and/or pH changes and a majority of the nanoparticles in the population maintain a diameter within a stated range (i.e., for example, between approximately 10-120 nm), the nanoparticle composition is stable. For some such populations, a majority is more than about 50%, 60%, 70%, 80%, 90%, 95%, 96%, 97%, 98%, 99%, 99.5%, 99.6%, 99.7%, 99.8%, 99.9% or more. In some embodiments of the invention, where a nanoparticle composition comprises botulinum toxin and/or at least one other biologically active agent, the nanoparticle composition is considered stable if the concentration of biologically active agent (e.g., botulinum toxin) is maintained in the composition over the designated period of time under a designated set of conditions.

As described herein, inventive nanoparticle compositions are useful in various medical, cosmetic, and nutraceutical applications. Such compositions may be delivered to a subject by any available route including, but not limited to injection, oral delivery, transdermal delivery, etc. In certain embodiments, the compositions are delivered by injection. In certain embodiments, the compositions are delivered transdermally.

It should be noted that inventive botulinum nanoparticle compositions are readily distinguishable from other botulinum-toxin-containing compositions that have been described. For example, Donovan has described a preparation in which botulinum toxin has been incorporated into a lipid vesicle for transdermal delivery (US Publication 2004/0009180). Such vesicles also require the incorporation of an enhancing agent, such as an alcohol, to facilitate the absorption of botulinum toxin through the skin. Donovan also describes a neurotoxin that is incorporated into a transfersome, which are deformable carriers containing lipids and membrane softeners (Hofer et al., 2000, World J. Surg., 24:1187; and U.S. Pat. No. 6,165,500). Donovan specifically describes the preparation of phosphatidyl choline+sodium cholate liposomes incorporating botulinum toxin.

Suvanprakorn et al. have also described suspensions of liposome-encapsulated materials in discrete macro-beads; one of the literally hundreds of compounds that is said to be amendable to encapsulation is "BOTOX®" (US Publication 2004/0224012). Included in contemplated methods of making these multi-lamellar vesicular liposomes are lyophilization/rehydration and organic solution dehydration/aqueous rehydration. These conventional methods of producing liposomes would be expected to produce microparticle-sized vesicles.

Methods of Making Nanoparticle Compositions

In general, inventive nanoparticle compositions (e.g., botulinum nanoparticle compositions) may be prepared by any available method. In some embodiments, nanoparticle compositions are prepared by chemical means. However, chemical means often require toxic (typically organic) solvents; in some embodiments, nanoparticle compositions are prepared in accordance with the present invention without utilizing such solvents.

In certain embodiments of the present invention, nanoparticle compositions are prepared by preparing a premix and subjecting the premix to high shear forces. As used herein, the term "shear force" refers to a force that is parallel to the face of a material, as opposed to a force that is perpendicular to the face of a material.

Any method known in the art can be used to generate high shear forces. In some embodiments, cavitation is used to generate high shear forces. According to the present invention, the use of mechanical energy (i.e., high shear forces) can replace or minimize any requirement to use costly and/or toxic chemical solvents; can increase the speed at which nanoparticles assemble; can increase the yield of nanoparticles generated in a particular mix of components, and/or can greatly reduce the overall cost of preparing nanoemulsion compositions. Furthermore, in those embodiments in which an agent such as a biologically active agent (e.g., botulinum toxin) is incorporated into inventive nanoparticle compositions, the use of high shear force can increase the loading capacity of the nanoparticle as compared to traditional methods of forming nanoparticles. In traditional methods, loading of agents within or on the surface of nanoparticles typically relies on diffusion of the agent to the interior and/or to the surface of the nanoparticle. According to the present invention, the use of high shear force can allow for the manufacture of smaller particles (e.g., on average) and/or a more narrow distribution of particle sizes in a nanoparticle composition.

In some embodiments, high shear forces are achieved by exposure to high pressure, for example by continuous turbulent flow at high pressure, for example about 15,000 psi. In some embodiments, such high pressure is within the range of about 18,000 to about 26,000 psi; in some embodiments, it is within the range of about 20,000 to 25,000 psi.

In some embodiments, high shear force or high pressure may be administered by cavitation or high pressure homogenization.

In some embodiments, high shear force may be administered by passage through an instrument such as, for example, a Microfluidizer® Processor (Microfluidics Corporation/ MFIC Corporation) or other like device. Microfluidizer® Processors provide high pressure and a resultant high shear rate by accelerating the product through microchannels to a high velocity for size reduction to the nanoscale range. The fluid is split in two and is pushed through microchannels with typical dimensions in the order of 75 microns at high velocities (in the range of 50-300 m/s). As the fluid exits the microchannels it forms jets which collide with jets from opposing microchannels. In the channels the fluid experiences high shear (up to $10^7$ 1/s) which is orders of magnitude higher than that of conventional technologies. Jet collisions result in mixing in submicron level. Therefore, high shear and impact are responsible for particle size reduction and mixing of multiphase fluids in the Microfluidizer® technology.

More generally, a "Microfluidizer®" may be any device that powers a single acting intensifier pump. The intensifier pump amplifies the hydraulic pressure to a selected level which, in turn, imparts that pressure to the product stream. As the pump travels through its pressure stroke, it drives the product at constant pressure through the interaction chamber. Within the interaction chamber are specially designed fixed geometry microchannels through which the product stream will accelerate to high velocities, creating high shear and impact forces that can generate a uniform nanoparticle composition (e.g., nanoemulsion) as the high velocity product stream impinges on itself and on wear-resistant surfaces.

As the intensifier pump completes its pressure stroke, it reverses direction and draws in a new volume of product. At the end of the intake stroke, it again reverses direction and drives the product at constant pressures, thereby repeating the process.

Upon exiting the interaction chamber, the product flows through an onboard heat exchanger which regulates the product to a desired temperature. At this point, the product may be recirculated through the system for further processing or directed externally to the next step in the process (U.S. Pat. Nos. 4,533,254; and 4,908,154).

In some embodiments of the present invention, a sample is "microfluidized" through exposure to high shear forces for a period of time less than about 10 minutes. In some embodiments, the period of time is less than about 9, 8, 7, 6, 5, 4, 3, 2, or 1 minute(s). In some embodiments, the period of time is within the range of about 1-2 minutes or less; in some embodiments, the period of time is about 30 seconds.

In some embodiments of the invention, a sample is "microfluidized" through a single exposure to high shear forces; such embodiments are referred to herein as "single pass" microfluidization.

The present invention encompasses the recognition that subjecting a premix to high shear forces can generate a nanoparticle composition, and in particular can generate a uniform nanoparticle composition.

In general, the premix from which inventive nanoparticle compositions are prepared through the application of high shear force is expected to contain at least two immiscible materials, one of which will constitute the dispersion medium (i.e., the liquid medium in which particles (e.g., nanoparticles) are dispersed in the ultimate nanoparticle composition). An "oil-in-water" dispersion is one in which oily particles are dispersed within an aqueous dispersion medium. A "water-in-oil" dispersion is one in which aqueous particles are dispersed within an oily dispersion medium. Those of ordinary skill in the art will appreciate that a dispersion can be formed from any two immiscible media and is not limited strictly to combinations of aqueous and oily media. The term "dispersion medium" therefore applies broadly to any dispersion medium notwithstanding that it is common to refer to "aqueous" and "oily" categories.

Thus, in some embodiments of the invention, the premix will contain an aqueous dispersion medium and an oily medium that becomes dispersed in nanoparticle form in the dispersion medium; in some embodiments of the invention, the premix contains an oily dispersion medium and an aqueous medium that becomes dispersed in nanoparticle form in the oily dispersion mediums.

Those of ordinary skill in the art will be well aware of suitable aqueous media that can be used as dispersion media or as media to be dispersed in accordance with the present invention. Representative such aqueous media include, for example, water, saline solutions (including phosphate buffered saline), water for injection, short chain alcohols, 5% dextrose, Ringer's solutions (lactated Ringer's injection, lactated Ringer's plus 5% dextrose injection, acylated Ringer's injection), Normosol-M, Isolyte E, and the like, and combinations thereof.

Those of ordinary skill in the art will also be well aware of suitable oily media that can be used as dispersion media or as media to be dispersed in accordance with the present invention. Representative such oily media include, for example, saturated and unsaturated almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils; butyl stearate; caprylic triglyceride; capric triglyceride; cyclomethicone; diethyl sebacate; dimethicone 360; isopropyl myristate; mineral oil; octyldodecanol; oleyl alcohol; silicone oil; and combinations thereof.

In addition to the two immiscible media, a premix according to the present invention may include, for example, one or more biologically active agents (e.g., botulinum toxin) and/or one or more surfactants or emulsifying agents. Suitable such surfactants or emulsifying agents include, but are not limited to, phosphoglycerides; phosphatidylcholines; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohols such as polyethylene glycol (PEG); polyoxyethylene-9-lauryl ether; a surface active fatty acid, such as palmitic acid or oleic acid; fatty acids; fatty acid monoglycerides; fatty acid diglycerides; fatty acid amides; sorbitan trioleate (Span 85) glycocholate; sorbitan monolaurate (Span 20); polysorbate 20 (Tween-20); polysorbate 60 (Tween-60); polysorbate 65 (Tween-65); polysorbate 80 (Tween-80); polysorbate 85 (Tween-85); polyoxyethylene monostearate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebrosides; dicetylphosphate; dipalmitoylphosphatidylglycerol; stearylamine; dodecylamine; hexadecyl-amine; acetyl palmitate; glycerol ricinoleate; hexadecyl sterate; isopropyl myristate; tyloxapol; poly(ethylene glycol)5000-phosphatidylethanolamine; poly(ethylene glycol)400-monostearate; phospholipids; synthetic and/or natural detergents having high surfactant properties; deoxycholates; cyclodextrins; chaotropic salts; ion pairing agents; and combinations thereof. The surfactant component may be a mixture of different surfactants. These surfactants may be extracted and purified from a natural source or may be prepared synthetically in a laboratory. In a preferred embodiment, the surfactants are commercially available.

In some embodiments of the present invention, all of the components present in the final nanoparticle composition are present in the premix and are subjected to high shear force to produce the nanoparticle composition. In some embodiments of the present invention, one or more of the components that are present in the final nanoparticle composition is/are missing from the premix or is/are present in the premix in a smaller amount than in the final nanoparticle composition. That is, in some embodiments of the present invention, one or more materials are added to the nanoparticle composition after the premix is subjected to high shear force.

In certain embodiments of the invention, the premix is prepared as a solution prior to application of high shear force. In particular, for nanoparticle compositions that include at least one biologically active agent (e.g., botulinum toxin), it is often desirable for the biologically active agent to be dissolved in the premix before the high shear force is applied. Thus, in many embodiments, the biologically active agent is soluble in at least one of the media (or in a combination of media utilized in the premix). In some embodiments of the invention, such dissolution requires heating; in other embodiments it does not.

In some embodiments of the present invention, the premix components may assemble into particles before the application of high shear force. At least some of such particles may be microparticles or even nanoparticles. In some embodiments, an inventive nanoparticle composition is prepared from a premix, wherein the premix is selected from the group comprising a suspension or a microemulsion. In some embodiments, however, particle structures do not form in the premix before application of high shear force.

In certain embodiments of the invention, relative amount of premix components are selected or adjusted to generate nanoparticles having desired characteristics. In some embodiments, the premix comprises oil and surfactant at a ratio ranging between 0.5-10. In some embodiments, the ratio of oil to surfactant is approximately 0.5:1, 1:1, 2:1, 3:1, 4:1, 5:1, 6:1, 7:1, 8:1, 9:1 or 10:1. In some embodiments, the ratio of surfactant to oil is approximately 0.5:1, 1:1, 2:1, 3:1, 4:1, 5:1, 6:1, 7:1, 8:1, 9:1 or 10:1. In some embodiments, the premix comprises oil and surfactant at a ratio ranging between 0.5-2. In some embodiments, the ratio of oil to surfactant is approximately 0.5:1, 1:1, or 2:1. In some embodiments, the ratio of surfactant to oil is approximately 0.5:1, 1:1, or 2:1. In certain embodiments, the ratio of oil to surfactant is approximately 1:1.

In some embodiments, the percent of oil in the premix ranges between 0%-30%. In some embodiments the percent of oil in the premix is 1%, 2%, 3%, 4%, 5%, 6%, 7%, 9%, 10%, 11%, 12%, 13%, 14%, 15%, 16%, 17%, 18%, 19%, 20%, 21%, 22%, 23%, 24%, 25%, 26%, 27%, 28%, 29% or 30%. In some embodiments the percent of oil is approximately 8%. In some embodiments the percent of oil is approximately 5%.

In some embodiments, the percent of surfactant in the premix ranges between 0%-30%. In some embodiments the percent of surfactant in the premix is 1%, 2%, 3%, 4%, 5%, 6%, 7%, 9%, 10%, 11%, 12%, 13%, 14%, 15%, 16%, 17%, 18%, 19%, 20%, 21%, 22%, 23%, 24%, 25%, 26%, 27%, 28%, 29% or 30%. In some embodiments the percent of surfactant approximately 8%. In some embodiments the percent of surfactant is approximately 5%.

In some embodiments, the nanoparticle composition does not contain more than one oil. In some embodiments, the nanoparticle composition may comprise two or more oils. In some embodiments, the nanoparticle composition does not contain more than one surfactant. In some embodiments, the nanoparticle composition may comprise two or more surfactants.

In some embodiments, the nanoparticle composition consists essentially of water, an oil, a surfactant, and a botulinum toxin. In some embodiments, the nanoparticle composition consists essentially of water, an oil, a surfactant, at least one botulinum toxin, and at least one substance used to produce and/or preserve the nanoparticle composition (e.g. proteins, salts, etc.).

In some embodiments, the nanoparticle composition consists of water, an oil, a surfactant, and a botulinum toxin. In some embodiments, the nanoparticle composition consists of water, an oil, a surfactant, at least one botulinum toxin, and at least one substance used to produce and/or preserve the nanoparticle composition (e.g. proteins, salts, etc.).

Methods of Administering Nanoparticle Compositions

The present invention provides methods of delivering nanoparticle compositions (e.g., botulinum nanoparticle compositions) for various applications including, for example, cosmetic, nutraceutical, and medical applications. Such nanoparticle compositions may include one or more biologically active agents. In many embodiments, the nanoparticle compositions include botulinum toxin.

In some embodiments, the present invention contemplates methods of delivering inventive nanoparticle compositions including, but not limited to transdermal, intramuscular, or subcutaneous routes of administration. These routes of administration are particularly favored for formulations (e.g., certain botulinum toxin nanoparticle compositions) that are intended to have a localized effect. Subsequent tissue absorption of the formulation's ingredients, however, is not always predictable.

In some embodiments of the present invention, inventive formulations may be encapsulated for example using lipid-based carriers, e.g., to facilitate entry into cells. Lipid-based carrier efficacies, however, may be dependent upon; i) lipid composition (i.e., for example, molecular size and charge); ii) the structure (e.g., molecular size and pH ionization) of any biologically active agent or other entity included in the composition; and iii) the overall health of the subject. The present invention contemplates compositions and methods related to uniform microfluidized nanoemulsions comprising either lipid-based carriers thereby improving the bioavailability of cosmeceuticals (i.e., for example, botulinum toxins).

The present invention specifically provides methods of administering botulinum toxin, and particularly of administering botulinum toxin nanoparticle compositions, for the treatment of various disorders, diseases, or conditions. Clinical effects of peripheral injection (i.e., intramuscular or subcutaneous), or topically applied transdermal administration, of botulinum toxins are usually seen within one week. The typical duration of symptomatic relief (i.e., for example, flaccid muscle paralysis) from a single intramuscular injection of botulinum toxin type A can be present for up to four months four months or longer; durations of clinical effect following transdermal administration of botulinum toxins according to the present invention can be present for up to four months or longer, depending on the characteristics of the individual subject and/or one the specific formulation of inventive botulinum nanoparticle preparation.

It will be appreciated by those of ordinary skill in the art that botulinum toxin is currently administered almost exclusively by injection, and in particular by injection of a liquid saline solution, usually reconstituted from a lyophilized preparation. As already discussed herein, botulinum toxin in the context of such preparations is especially vulnerable to instability resulting in a loss of protein and/or loss of protein activity. Such instability is suspected to a result of protein denaturation, degradation, dimerization, and/or polymerization. The most common formulation known to have botulinum stabilizing effects is human albumin. The possible immunological consequences of human-derived albumin have recently been discussed (US Publication 2005/0238667). This publication proposes that recombinant albumin's, saccharide-based stabilizers, and anti-oxidant amino acids may result in botulinum toxins having an improved efficacy relative to native albumin preparations.

As has also already been discussed, BOTOX® (a purified *Clostridium botulinum* toxin type A complex, human serum albumin, and sodium chloride packaged in a sterile vacuum-dried form) is currently reconstituted for injection using sterile normal saline without a preservative (0.9% sodium chloride, injection grade). Specifically, standard injection protocols involve drawing up the proper amount of diluent in the appropriate size syringe. Since BOTOX® is denatured by bubbling or similar violent agitation, the diluent is gently injected into a vial containing a designated amount of lyophilized BOTOX®. For sterility reasons, standard injection protocols involve administering aqueous BOTOX® solutions within four hours after reconstitution.

Although problems with the available botulinum toxin preparations (including stability issues, sterility issues, etc.) have been well known, few improved formulations have been developed. Furthermore, injection remains the standard approach for delivering botulinum toxin, notwithstanding the undesirability of invasive techniques generally, patient discomfort, etc.

The present invention provides improved botulinum toxin compositions (e.g., botulinum toxin nanoparticle compositions), and further provides improved methods of delivering botulinum toxin. In particular, the present invention provides methods of delivering botulinum nanoparticle compositions (by any available route), and further provides methods of delivering botulinum toxin by routes other than injection.

In general, inventive botulinum nanoemulsion compositions may be administered by any available means including, without limitation, parenterally, orally, transdermally, bucally, opthalmically, vaginally, rectally, etc. In certain embodiments, however, the compositions are administered by injection; in some embodiments by subcutaneous injection, in some embodiments by intramuscular injection, in some embodiments by intravenous injection, etc. In certain embodiments, inventive botulinum nanoparticle compositions are administered transdermally.

In certain embodiments, the present invention provides methods of administering botulinum toxin transdermally. Human skin comprises the dermis and the epidermis. The epidermis has several layers of tissue, namely, stratum corneum, stratum lucidum, stratum granulosum, stratum spinosum, and stratum basale (identified in order from the outer surface of the skin inward).

The stratum corneum presents the most significant hurdle in transdermal delivery of medications generally, and presumably of botulinum toxin in particular. The stratum corneum is typically about 10-15 µm thick, and it consists of flattened, keratised cells (corneocytes) arranged in several layers. The intercellular space between the corneocytes is filled with lipidic structures, and may play an important role in the permeation of substances through skin (Bauerova et al., 2001, *European Journal of Drug Metabolism and Pharmacokinetics*, 26:85).

The rest of the epidermis below the stratum corneum is approximately 150 µm thick. The dermis is about 1-2 mm thick and is located below the epidermis. The dermis is innervated by various capillaries as well as neuronal processes.

Transdermal administration of pharmaceuticals generally has been the subject of research in attempt to provide an alternative route of administration of medications without undesirable consequences associated with injections and oral delivery. For example, needles often cause localized pain, and potentially expose patients receiving injections to blood borne diseases. Oral administration often suffers from poor bioavailability of medications due to the extremely acidic environment of the patient's stomach.

Efforts have been made to develop transdermal administration techniques for certain pharmaceuticals in an attempt to overcome these shortcomings by providing noninvasive administration. It is generally desirable with transdermal administration to reduce damage to a patient's skin. Thus, transdermal administration of medication may reduce or eliminate pain associated with injections, reduce the likelihood of blood contamination, and improve the bioavailability of drugs once they are incorporated systemically.

Traditionally, attempts at transdermal administration of medication have been focused in increasing the permeability of the stratum corneum. Some attempts have included using chemical enhancing agents that increase the permeability of molecules through the skin. Some attempts have included using mechanical apparatus to bypass or ablate portions of the stratum corneum. In addition, attempts have included use of ultrasound or iontophoresis to facilitate the permeation of pharmaceuticals through the skin. In most cases, the goal has been to a pharmaceutical agent, typically a small molecule, through the skin, typically so that an agent may pass to the capillary bed in the dermis where the agent may be systemically incorporated into the subject to achieve a therapeutic effect.

Although small molecules have been a major focus of transdermal administration techniques, it is important to note that it appears that large molecules, such as polypeptides, and protein complexes, are also amenable to transdermal administration. Erythropoietin, which is about 48 kD, has also been successfully transdermally administered with the assistance of ultrasound (Mitragotri et al., 1995, *Science,* 269:850; and U.S. Pat. Nos. 5,814,599 and 6,002,961).

The present invention provides, among other things, methods of administering botulinum toxin transdermally that do not require use of abrasive or other disrupting agents (whether chemical, mechanical, electrical, magnetic, etc.). Rather, the present inventors have surprisingly found that botulinum toxin incorporated into inventive nanoparticle compositions is effectively delivered transdermally without further steps to permeabilize or disrupt the stratum corneum. Use of such agents or steps with inventive botulinum nanoparticle compositions is not necessarily precluded in all embodiments of the present invention, but also is not required.

The present invention therefore provides methods of administering botulinum toxin through the topical application of an inventive botulinum nanoparticle composition. In some embodiments, the inventive botulinum nanoparticle composition is applied directly to the skin and for absorption through the epidermal layers. In some embodiments, the botulinum nanoparticle composition can penetrate the top layer of the skin, including the stratum corneum, dermal pores, and/or dermal glands, without the use of chemical or mechanical skin permeation enhancers or other agents that cause abrasion.

It will be appreciated by those of ordinary skill in the art that inventive compositions for topical administration may have a cosmetic formulation such as skin softener, nutrition lotion type emulsion, cleansing lotion, cleansing cream, skin milk, emollient lotion, massage cream, emollient cream, make-up base, lipstick, facial pack or facial gel, cleaner formulation such as shampoos, rinses, body cleanser, hair-tonics, or soaps, or dermatological composition such as lotions, ointments, gels, creams, patches or sprays.

An inventive composition for topical administration may be formulated and/or administered such that an amount of botulinum toxin between about $10^{-3}$ U/kg and 10 U/kg passes through a patient's skin. In some embodiments, the composition is formulated and/or administered so that between about $10^{-2}$ U/kg and about 1 U/kg transdermally pass through the patient's skin. In some embodiments, the composition is formulated and/or administered so that between about $10^{-1}$ U/kg and about 1 U/kg pass through the patient's skin. In some embodiments, the composition is formulated and/or administered so that between about 0.1 units and about 5 units pass through the patient's skin to a subdermal target.

Those of ordinary skill in the art will appreciate that units herein relate to Units that are biologically equivalent or bioactively equivalent to Units defined by commercial manufacturers of botulinum toxin.

The therapeutic effects of botulinum toxin administered according to the present invention may persist as long as do the effects of injected solution. The effects of such injected solution can persist for up to about 4 months. Furthermore, use of a synthetic polymer carrier that can retain the botulinum toxin so that it is released slowly may prolong the effects for up to about five years (U.S. Pat. No. 6,312,708).

In one embodiment, the present invention provides a topical formulation of botulinum toxin that avoids potential complications including, but not limited to, systemic toxicity or botulism poisoning. In one embodiment, dosages of botulinum toxin (including types A, B, C, D, E, F, or G) can range from as low as about 1 unit to as high as about 20,000 units, with minimal risk of adverse side effects. The particular dosages may vary depending on the condition being treated and therapeutic regime being utilized. For example, treatment of subdermal, hyperactive muscles may require high transdermal dosages (e.g., 1000 units to 20,000 units) of botulinum toxin. In comparison, treatment of neurogenic inflammation or hyperactive sweat glands may require relatively small transdermal dosages (e.g. about 1 unit to about 1,000 units) of botulinum toxin.

One embodiment of the present invention contemplates a pharmaceutical composition comprising a stabilized botulinum toxin for transdermal delivery into a human patient. The botulinum toxin can be selected from the group consisting of botulinum toxin types A, B, $C_1$, D, E, F and G, an isolated and/or purified (i.e. about 150 kD) botulinum toxin, as well as a native or recombinantly made botulinum toxin. The composition can comprise between about 1 unit to about 20,000 units of the botulinum toxin, and the composition can comprises an amount of botulinum toxin sufficient to achieve a therapeutic effect lasting between 1 month and 5 years.

In some embodiments, the present invention provides topical formulations of botulinum toxin (e.g., of botulinum nanoparticle compositions) that allow the botulinum toxin to permeate through a subject's skin without permeating in significant amount through a blood vessel. For example, in some embodiments of the invention, less than about 25%, or even less than about 5% of the botulinum toxin present in the pharmaceutical composition permeates into a blood vessel upon application of an inventive topical and/or transdermal preparation.

Those of ordinary skill in the art will appreciate that inventive compositions that achieve transdermal administration of botulinum toxin may be incorporated into a device such as, for example, a patch.

A variety of transdermal patch structures are known in the art; those of ordinary skill will appreciate that inventive botulinum nanoparticle compositions may readily be incorporated into any of a variety of such structures. In some embodiments, a transdermal patch may further comprise a plurality of needles extending from one side of the patch that is applied to the skin, wherein the needles extend from the patch to project through the stratum corneum of the skin. In some embodiments, the needles do not rupture a blood vessel.

In some embodiments of the present invention, botulinum toxin (e.g., a botulinum nanoparticle composition) can be provided in a depot in the patch so that pressure applied to the patch causes botulinum toxin to be directed out of the patch (optionally through needles) and through the stratum corneum.

In some embodiments of the present invention, a transdermal patch includes an adhesive. Some examples of adhesive patches are well known (for example, see U.S. Pat. Nos. Des. 296,006; 6,010,715; 5,591,767; 5,008,110; 5,683,712; 5,948, 433; and 5,965,154). Adhesive patches are generally characterized as having an adhesive layer, which will be applied to a person's skin, a depot or reservoir for holding a pharmaceutical agent, and an exterior surface that prevents leakage of the pharmaceutical from the depot. The exterior surface of a patch is typically non-adhesive.

In accordance with the present invention, the neurotoxin is incorporated into the patch so that the neurotoxin remains stable for extended periods of time. For example, the neurotoxin may be present in an inventive botulinum nanoparticle composition. Alternatively or additionally, the neurotoxin may be incorporated into a polymeric matrix that stabilizes the neurotoxin, and permits the neurotoxin to diffuse from the matrix and the patch. The neurotoxin may also be incorporated into the adhesive layer of the patch so that once the patch is applied to the skin, the neurotoxin may diffuse through the skin. In one embodiment, the adhesive layer may be heat activated where temperatures of about 37° C. cause the adhesive to slowly liquefy so that the neurotoxin diffuses through the skin. The adhesive may remain tacky when stored at less than 37° C., and once applied to the skin, the adhesive loses its tackiness as it liquefies. The administration of the toxin is complete once the patch no longer adheres to the skin.

Those of ordinary skill in the art will appreciate that a transdermal patch is but one example of a device with which inventive botulinum nanoparticle compositions may be administered. To give but a few other examples, a device may be employed that allows the composition to be applied without first applying the composition to one's fingers, which may lead to undesirable paralysis of the fingers. Suitable devices include spatulas, swabs, syringes without needles, and adhesive patches. Use of spatulas or swabs, or the like may require the device to be inserted into a container containing the composition. Using syringes may be accomplished by filling the syringe with the composition. The composition may then be topically spread by the spatulas or swabs, or may be expelled from the syringes onto the person's skin.

In many embodiments of the invention, it may be desirable to limit delivery of botulinum toxin to only an intended delivery area. In some embodiments, such limited delivery may be accomplished by utilizing an inventive botulinum nanoparticle composition in an application device that permits application of the composition to a target site on the skin without applying the composition to non-target site areas of the skin. Clearly, a transdermal patch may be utilized to this end. Alternatively or additionally, if botulinum toxin is to be applied topically to only a selected area, other areas may be covered or pre-treated or otherwise protected from exposure.

Treatment Applications of Botulinum Toxin

As described herein, many embodiments of the present invention involve delivery of botulinum toxin to a subject in the context of a nanoparticle composition. Such delivery is useful in a variety of contexts, including in particular certain cosmetic and medical applications. Certain such applications are discussed in more detail below.

Cosmetic Applications

Botulinum toxin A (BTXA) has become a widely used drug in cosmetic dermatology. Adverse effects of BTXA observed with cosmetic use have a significant impact on patient compliance. Currently, BTXA is administered by medical personnel and in a clinical setting both because BTXA is administered by injection, which requires trained personnel, and because the major tools for preventing adverse effects from BTXA are knowledge and skill. Use of correct injection techniques is mandatory since most unwanted effects are caused by incorrect technique. Knowledge of human anatomy, (i.e., for example, facial and extrafacial muscles), is important for physicians to select the optimal dose, time and technique.

The most common adverse effects of current procedures for administering BTXA are pain and hematoma. For example, when BTXA solution is administered by injection to the periocular region, eyelid and brow ptosis are common adverse effects. Adverse effects such as pain, hematoma, ecchymosis, and bruising may also occur in the upper and lower face and at extrafacial sites. Other possible adverse effects include, but are not limited to, headache and possible interaction with concomitant medications. Suggestions have been made to avoid the most unwanted adverse effects by implementing the proper techniques of dilution, storage, and injection, as well as the careful exclusion of patients with any contraindications. Pain, hematoma, ecchymosis, and bruising can be prevented by cooling the skin before and after BTXA injection. Upper lid ptosis may be partly corrected using apraclonidine or phenylephrine eyedrops (Wollina et al., 2005, Am. J. Clin. Dermatol., 6:141). However, significant adverse effects remain with current strategies.

By contrast, the present invention provides methods and compositions for safely and effectively administering botulinum toxins in a manner that minimizes adverse side effects. In one embodiment, the present invention contemplates method of botulinum administration as a topically and/or locally delivered composition comprising a nanoparticle composition such as a microfluidized nanoemulsion. In one embodiment, the composition is formulated as a cream, ointment, oil, foam, spray, or gel.

Those of ordinary skill in the art will appreciate that inventive botulinum nanoparticle compositions may be formulated together with any of a variety of cosmetically acceptable media in cosmetic preparations such as liquids, creams, emulsions, gels, thickening lotions, or powders; they can contain water and also any cosmetically acceptable solvent, in particular, monoalcohols, such as alkanols having 1 to 8 carbon atoms (like ethanol, isopropanol, benzyl alcohol and phenylethyl alcohol), polyalcohols, such as alkylene glycols (like glycerine, ethylene glycol and propylene glycol), and glycol ethers, such as mono-, di-, and tri-ethylene glycol monoalkyl ethers, for example, ethylene glycol monomethyl ether and diethylene glycol monomethyl ether, used singly or in a mixture. Such components can be present, for example, in proportions of up to as much as 70% by weight, relative to the weight of the total composition.

Cosmetic preparations including inventive botulinum nanoparticle compositions may contain at least one filler, especially in order to obtain a matte product, which is especially desired for individuals with greasy skin. The term "filler" means any particle that is solid at room temperature and atmospheric pressure, used alone or in combination, which does not react chemically with the various ingredients of the composition and which are insoluble in these ingredients, even when these ingredients are brought to a temperature above room temperature and especially to their softening point or to their melting point. Such inert fillers typically have melting points at least higher than 170° C., and better still higher than 200° C.

Fillers may be absorbent or nonabsorbent, i.e. capable in particular of absorbing the oils of the composition and also the biological substances secreted by the skin. In some embodiments, fillers are particulate and have an apparent diameter ranging from 0.01 to 150 µm, preferably from 0.5 to 120 µm and better still ranging from 1 to 80 µm. An apparent diameter corresponds to the diameter of the circle in which the elementary particle is inscribed along its smallest dimension (thickness for lamellae).

Treatment of Wrinkles

Facial wrinkles involving the forehead, glabellar, rhytids and/or periorbital regions are a common aesthetic problem and are believed related to overactivity of the underlying facial musculature. For instance, the development of glabellar wrinkles is related, at least in part, to the dynamics of the underlying procerus, corrugator supercilii, and orbicularis oculi muscles. Facial lines are considered problematic because they produce the appearance of aging. In some cases, they can also be misinterpreted as manifestations of negative emotions (e.g., anger, anxiety, sadness), fatigue, or stress.

In recent years, injections of botulinum toxin solutions have become one of the most popular therapies for the treatment of hyperfunctional facial lines. After injection, the toxin acts to paralyze or weaken facial mimetic muscles. This apparently reduces or eliminates the appearance of wrinkles. Sadick N S., "The cosmetic use of botulinum toxin type B in the upper face" Clin Dermatol. 22(1):29-33 (2004).

The initial cosmetic use of a botulinum toxin solution was for treatment of forehead frown lines (Carruthers et al., 1992, *J. Dermatol. Surg Oncol.*, 18:17). It has also been noted that injection of BTX solution into the platysma produces an uplift of the mouth (Brandt et al., 1998, *Dermatol. Surg.*, 24:1232). Injection of BTX solution into the point of the chin has also been done for treatment of prominent mental crease (Carruthers et al., "Cosmetic Uses of Botulinum A Exotoxin," pp. 325-48, *Advances in Dermatology*, James, et al., eds., Mosby-Yearbook, Chicago, 1997).

The present invention provides nanoparticle compositions for the treatment of facial wrinkles and/or unsightly facial expressions (e.g., due to overactivity of underlying facial musculature). Of course, the principles and/or compositions relevant to the treatment of facial wrinkles and/or expressions may equally be applied to undesirable lines or wrinkles caused by muscle activity elsewhere in the body (e.g., neck lines, etc.). In some embodiments, inventive nanoparticle compositions for use in treating wrinkles comprise one or more neuroparalytic toxins; in some embodiments such toxins are capable of blocking facial muscle activity; in some embodiments, such toxins comprise botulinum toxin (BTX). In some embodiments, the present invention contemplates administration of a microfluidized botulinum toxin nanoemulsion to facial wrinkles.

It has been recently been suggested that the onset of facial wrinkles and/or lines can be delayed by the long-term use of botulinum type A toxin treatment via repeated injections (Binder, 2006, *Arch. Facial Plast. Surg.*, 8:426). However, repeated injections are painful to the patient, and there is a risk of injecting unintended muscle groups, potentially causing adverse side-effects (e.g. ptosis). In some embodiments, a botulinum nanoemulsion is applied to the face and/or neck over an extended period of time to delay the onset of facial (or neck) lines or wrinkles. In some embodiments, a botulinum nanoemulsion is applied at regular intervals to the face and/or neck over an extended period of time to delay the onset of facial lines or wrinkles. In some embodiments, a botulinum toxin is applied at regular intervals to the face and/or neck over a period of time greater than 6 months to delay the onset of facial lines or wrinkles. In some embodiments, a botulinum toxin is applied at regular intervals to the face and/or neck over a period of time greater than 1 year to delay the onset of facial lines or wrinkles. In some embodiments, a botulinum toxin is applied at regular intervals to the face and/or neck over a period of time greater than 5 years to delay the onset of facial lines or wrinkles. In some embodiments, a botulinum toxin is applied at regular intervals to the face and/or neck over a period of time greater than 10 years to delay the onset of facial lines or wrinkles.

Hyperkinetic Facial Lines

Injection of Botulinum toxin type B (BTX-B) has been evaluated in the management of hyperfunctional facial lines. For example, twenty-four patients were treated with 400 to 800 units BTX-B in the corrugator, orbicularis oculi, or frontalis muscle. Facial line improvements may be evaluated using the Wrinkle Improvement Score (WIS) and Rated Numeric Kinetic Line Scale (RNKLS). One study reported an onset of effect was within 72 hours. WIS and RNKLS for all sites were statistically better after treatment, with the effect lasting 8 weeks. In general, patients noted a moderate improvement (grade 2) on WIS and a 2-point improvement on RNKLS (Ramirez et al., 2002, *Otolaryngol. Head Neck Surg.*, 126:459).

In some embodiments, the present invention contemplates administration of a botulinum nanoparticle composition such as a microfluidized botulinum toxin nanoemulsion to hyperkinetic facial lines. In some embodiments, the present invention contemplates administration of a botulinum nanoparticle composition to regions of the face that typically develop wrinkles prior to wrinkle formation. It is expected that repeated such administration may delay onset of and/or reduce intensity or severity of wrinkles that may ultimately develop (Binder, 2006, *Arch. Facila Plast. Surg.*, 8:426).

Platysma Bands

The platysma is a broad thin layer of muscle that is situated on each side of the neck immediately under the superficial fascia belonging to the group of facial muscles, that is innervated by the facial nerve, and that draws the lower lip and the corner of the mouth to the side and down and when moved forcefully expands the neck and draws its skin upward.

Injection of botulinum toxin Z has been reported to treat sagging hypertrophic platysma muscle bands (i.e., typically referred to as the aging neck). A classification system (I to IV) based on horizontal neck rhytids, platysma bands, and skin laxity can categorize the degree of deformity and serve as a guideline for suggested dosages of botulinum. For example: Type II refers to mild horizontal neck rhytids; thin, mild platysma muscle flaccidity; and mild skin laxity; Type III refers to moderate horizontal neck rhytids; thick, moderate platysma muscle flaccidity; and moderate skin laxity (Matarasso et al., 1999, *Plast. Reconstr. Surg.*, 103:645).

In one embodiment, the present invention contemplates administration of a botulinum nanoparticle composition such as a microfluidized botulinum toxin nanoemulsion to platysma bands.

Medical Applications

Neuromuscular Disorders

BTX produced by the bacterium *Clostridium botulinum* reversibly paralyzes striated muscle when administered in sub-lethal doses. BTX has been used in the treatment in a number of neuromuscular disorders and conditions involving muscular spasm and/or contracture including various forms of palsy, facial contracture, dystonia, hemifacial spasm, tremor, spasticity (e.g. resulting from multiple sclerosis), retroorbital muscle, and various other ophthalmologic conditions (Carruthers et al., 1996, *J. Am. Acad. Dermatol.*, 34:788).

Facial Palsy

It has been reported that injection of BTX into a group of muscles on one side of a patient's face has been used to treat facial synkinesis and vertical asymmetry caused by facial nerve palsy (Armstrong et al., 1996, *Clin. Otolaryngol.*, 21:15). In the latter procedure, the levator anguli oris, zygomaticus major, rizorius and depressor anguli oris muscles associated with the mouth together with various muscles associated with the eye on the normal side of a patient's face were all treated as a group in order to affect the entire vertical symmetry of a patient's face to compensate for effects of nerve palsy on the untreated side of the face.

In one embodiment, the present invention contemplates administration of a botulinum nanoparticle composition such as a microfluidized botulinum toxin nanoemulsion to spastic facial muscles.

Blepharospasm

Blepharospasm is diagnosed in response to repeated and rhythmic contraction of the eyelid muscles (i.e., also known as eyelid spasm). In some instances, the eyelid may repeatedly close (or nearly close) and re-open. The origination of this condition commonly results from fatigue, stress, and/or caffeine. Once spasms begin, however, they may continue off and on for a few days.

More severe contractions, where the eyelid completely closes, are possible. This aggravated condition can be caused by irritation of the surface of the eye (cornea) or the membranes lining the eyelids (conjunctiva). This form of eyelid twitching lasts much longer, is often very uncomfortable, and can also cause your eyelids to close completely.

Symptoms of blepharospasm include, but are not limited to, a repetitive, uncontrollable twitching or spasms of your eyelid (usually the upper lid), light sensitivity, or blurry vision.

In some embodiments, the present invention contemplates administration of a botulinum nanoparticle composition such as a microfluidized botulinum toxin nanoemulsion to the eyelid muscle.

Cerebral Palsy

Cerebral palsy includes a group of disorders characterized by loss of movement or loss of other nerve functions. These disorders are caused by injuries to the brain that occur during fetal development or near the time of birth. Cerebral palsy may be caused by injury to the cerebrum (the largest portion of the brain, which is involved with higher mental faculties, sensations, and voluntary muscle activities).

Injury to the cerebrum can result in the loss of nerve functions in widely different areas. The classical finding of CP is spasticity (increased muscle tone) which may affect a single limb, one side of the body (spastic hemiplegia), both legs (spastic diplegia) or both arms and legs (spastic quadriplegia). In addition, there may be partial or full loss of movement (paralysis), sensory abnormalities, and defects of hearing and vision. Speech abnormalities are common and seizures may occur.

Intellectual function in CP patients may range from extremely bright normal to severe mental retardation. Symptoms are usually evident before age 2 and in severe cases may appear as early as 3 months. Cerebral palsy is a non-progressive type of encephalopathy (injury to the brain) and symptoms directly resulting from the disease do not worsen.

Classifications of cerebral palsy include spastic, dyskinetic, ataxic, and mixed. Spastic cerebral palsy includes about 50% of cases. Dyskinetic (athetoid) cerebral palsy affects about 20%. It involves development of abnormal movements (twisting, jerking, or other movements). Ataxic cerebral palsy involves tremors, unsteady gait, loss of coordination, and abnormal movements. It affects about 10%. The remaining 20% are classified as mixed, with any combination of the above symptoms.

Symptoms of cerebral palsy include, but are not limited to, seizures, muscle contractions, difficulty sucking or feeding, irregular breathing, delayed development of motor skills, such as reaching, sitting, rolling, crawling, walking, motor-mental retardation, mental retardation, speech abnormalities (dysarthria), visual abnormalities, hearing abnormalities, spasticity, progressive joint contractures, limited range of motion, or peg teeth.

Botulinum toxins are effective in treating the child with cerebral palsy and other hypertonias by decreasing deformity, promoting function, improving motor control, and elongation of shortened muscles. For children with focal hypertonia, botulinum toxins offer a dramatic but temporary repeatable change that affects rehabilitation. Research rapidly has captured the positive effect of the toxins on impairment and functional limitations. The long-term use of botulinum toxins and the role the toxins play throughout the life span of the person with a childhood hypertonic disorder are yet to be determined (Gaebler-Spira et al., 2003, *Phys. Med. Rehabil. Clin. N. Am.,* 14:703).

In one embodiment, the present invention contemplates administration of a botulinum nanoparticle composition such as a microfluidized botulinum toxin nanoemulsion to a patient exhibiting symptoms of hypertonia. In one embodiment, the hypertonia comprises cerebral palsy. In one embodiment, the patient is a child.

Strabismus

Strabismus involves deviation of the alignment of one eye in relation to the other and is also referred to as crossed eyes, esotropia, exotropia, squint or walleye. It is believed that strabismus is caused by a lack of coordination between the eyes. As a result, the eyes look in different directions and do not focus simultaneously on a single point.

In most cases of strabismus in children, the cause is unknown. In more than half of these cases, the problem is present at or shortly after birth (congenital strabismus). When the two eyes fail to focus on the same image, the brain may learn to ignore the input from one eye. If this is allowed to continue, the eye that the brain ignores will never see well. This loss of vision is called amblyopia, and it is frequently associated with strabismus.

Acquired strabismus in adults can be caused by injuries to the orbit of the eye or brain, including closed head injuries and strokes. People with diabetes often have loss of circulation causing an acquired paralytic strabismus. Loss of vision in one eye from any cause will usually cause the eye to gradually turn outward (exotropia). Because the brains of adults are already developed for vision, the problems associated with amblyopia, in which the brain ignores input from one eye, do not occur with adult strabismus.

Symptoms of strabismus include, but are not limited to, eyes that appear crossed, eyes that do not align in the same direction, uncoordinated eye movements, double vision, or vision in only one eye with loss of depth perception.

Long-term results of botulinum therapy in patients having acquired esotropia have been reported. Sixty-eight children (age range, 8-64 months) with acquired esotropia were enrolled in a prospective study. Botulinum toxin A was injected in the two medial recti. Motor and sensory statuses were evaluated at 1 and 2 weeks; 3, 6, and 12 months; and every year after the last injection.

After an average follow-up of 4.8 years since the last injection, motor success was obtained in 36 children with one injection (52.9%), increasing to 48 (70.6%) and 60 (88.2%) children after two and three injections, respectively. Forty-eight (70.6%) patients had at least peripheral fusion (category 1 binocularity) and 32 (47.1%) had stereoacuity of at least 400 seconds of arc (category 2 binocularity). Higher hypermetropia, less severe amblyopia, and a smaller angle of esotropia were the best predictors of motor success. Minimal amblyopia and favorable motor alignment were associated with better binocularity outcome.

Botulinum toxin may be an effective long-term treatment of acquired esotropia. It is especially useful in children with high hypermetropia, minimal amblyopia, and small esotropic deviation (Tejedor et al., 2001, *Investigative Ophthalmology and Visual Science,* 42:2542).

In one embodiment, the present invention contemplates administration of a botulinum nanoparticle composition such as a microfluidized botulinum toxin nanoemulsion to a patient exhibiting symptoms of strabismus. In one embodiment, the patient is a child.

Dystonia

Dystonia is a medical condition comprising involuntary slow and twisting movements. An uncontrolled or slow movement is defined as an impairment of the muscle tone (usually in large muscle groups), causing slow involuntary contractions of the head, limbs, trunk, or neck (i.e., cervical dystonia). The slow sinuous twisting movements of muscles (athetosis) or sustained muscle contraction (dystonia) may be caused by a number of conditions, including cerebral palsy, encephalitis, drug side effects, hepatic encephalopathy, and Huntington's chorea. The abnormal movement may be reduced or disappear during sleep, but it is worsened by emotional stress. Abnormal and sometimes grotesque postures may be a manifestation of these movements.

In one embodiment, the present invention contemplates administration of a botulinum nanoparticle composition such as a microfluidized botulinum toxin nanoemulsion to a patient exhibiting symptoms of dystonia.

Prostate Hyperplasia

Botulinum toxin injection may be effective in men with benign prostatic hyperplasia. Thirty men with benign prostatic hyperplasia were enrolled in a randomized, placebo-controlled study. After a baseline evaluation, each participant received 4 mL of solution injected into the prostate gland. Patients in the control group received saline solution and patients in the treated group received 200 U of botulinum toxin A. The outcome of each group was evaluated by comparing the symptom scores, serum prostate-specific antigen concentration, prostate volume, postvoid residual urine volume, and peak urinary flow rates.

After 2 months, 13 patients in the treated group and 3 in the control group had subjective symptomatic relief (P=0.0007). In patients who received botulinum toxin, the symptom score was reduced by 65% compared with baseline values and the serum prostate-specific antigen concentration by 51% from baseline. In patients who received saline, the symptom score and serum prostate-specific antigen concentration were not significantly changed compared with the baseline values and 1-month values. Follow-up averaged 19.6+/−3.8 months (Maria et al., 2003, *Urology* 62:259).

In one embodiment, the present invention contemplates administration of a botulinum nanoparticle composition such as a microfluidized botulinum toxin nanoemulsion to a patient exhibiting symptoms of prostate hyperplasia.

Hyperhidrosis

Hyperhidrosis is a medical condition in which a person sweats excessively and unpredictably. People with hyperhidrosis can sweat even when the temperature is cool, and when they are at rest. Sweating helps the body stay cool and is perfectly natural. People sweat more in warm temperatures, when they exercise, or in response to situations that make them nervous, angry, embarrassed, or afraid.

However, excessive sweating occurs without such triggers. Those with hyperhidrosis appear to have overactive sweat glands. The uncontrollable sweating can lead to significant discomfort, both physical and emotional. When excessive sweating affects the hands, feet, and armpits, it's called primary or focal hyperhidrosis. Primary hyperhidrosis affects 2%-3% of the population, yet less than 40% of patients with this condition seek medical advice. In the majority of primary hyperhidrosis cases, no cause can be found. It seems to run in families. If the sweating occurs as a result of another medical condition, it is called secondary hyperhidrosis. The sweating may be all over the body, or it may be localized to one area. Conditions that cause second hyperhidrosis include but are not limited to, acromegaly, hyperthyroidism, glucose control disorders, pheochromocytoma, carcinoid syndrome, cancer, tuberculosis, infections, menopause, spinal cord injury, stroke, Parkinson's disease, heart or lung disease, medications, substances of abuse, or anxiety conditions. The primary symptom of hyperhidrosis is wetness.

Botulinum toxin type A (BOTOX®) was approved by the FDA in 2004 for the treatment of severe underarm sweating, a condition called primary axillary hyperhidrosis. Small doses of purified botulinum toxin injected into the underarm temporarily block the nerves that stimulate sweating. Side effects include injection-site pain and flu-like symptoms. BOTOX® used for sweating of the palms can cause mild, but temporary weakness and intense pain.

In one embodiment, the present invention contemplates administration of a botulinum nanoparticle composition such as a microfluidized botulinum toxin nanoemulsion to a patient exhibiting symptoms of hyperhidrosis.

EXEMPLIFICATION

The following examples are only intended to provide illustrations of specific embodiments contemplated by the present invention. The examples are not intended in any way to be limiting.

Example 1

Botulinum Nanoemulsion Formulation

This example presents one embodiment of nanoemulsion prepared by microfluidization comprising botulinum toxin (i.e., for example, BOTOX®).

A preparation for microfluidization was made as follows:

1. 5 g of soybean oil and 5 g of Tween 80 were mixed, heating as needed (typically not required) to emulsify the mixture.
2. 100 Units of BOTOX®, incorporated within a human albumin matrix (Allergan, Irvine Calif.), was added to 100 mL of deionized/distilled water and stirred until evenly mixed.
3. Step 1 preparation was added to Step 2 preparation and stirred until evenly mixed.
4. Preparation was homogenized for 1 minute (see resulting particle distributions in Table 1 and FIG. 1)
5. Single-pass microfluidization procedure at 24,000 psi was performed using a Microfluidizer® Processor.

Figure 2:
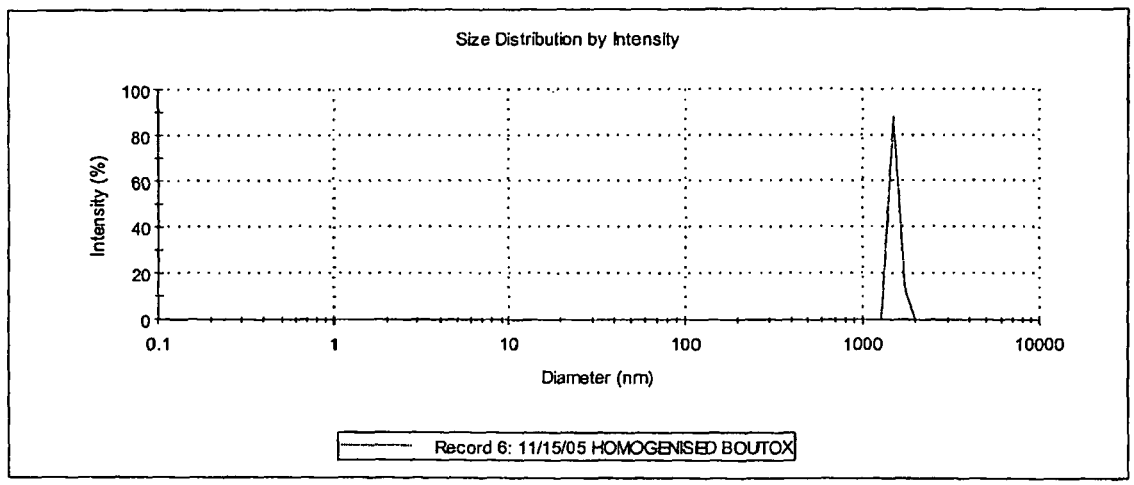
FIG. 2 shows one embodiment of a particle diameter distribution of homogenized botulinum toxin microemulsion.

The resulting nanoemulsion was evaluated for particle size using the Malvern Nano S particle sizer capable of sizing particles between about 0.6 nm-6000 nm. The BOTOX® nanoemulsion preparation had two particle size peaks having an average particle size of 95.33 nm (Table 2 and FIG. 2).

TABLE 1

Particle Size Distribution of a Homogenized BOTOX ® Microemulsion

|  |  | Diam. (nm) | % Intensity | Width (nm) |
|---|---|---|---|---|
| Z-Average: 3391 | Peak 1 | 1512 | 100 | 76.6 |
| PDI: 0.341 | Peak 2 | 0 | 0 | 0 |
| Intercept: 0.5852 | Peak 3 | 0 | 0 | 0 |

TABLE 2

Particle Size Distribution of a Microfluidized BOTOX ® Nanoemulsion

|  |  | Diam. (nm) | % Intensity | Width (nm) |
|---|---|---|---|---|
| Z-Average: 95.33 | Peak 1 | 134.2 | 76.49 | 31.03 |
| PDI: 0.252 | Peak 2 | 44.97 | 23.51 | 6.34 |
| Intercept: 0.9659 | Peak 3 | 0 | 0 | 0 |

Example 2

Muscle Relaxant Effect of Injected BOTOX® Nanoemulsions

This example presents one embodiment of BOTOX® nanoemulsions that have comparable efficacy as free solution BOTOX® injections as a saline solution.

The experimental design compared the following two BOTOX® preparations:
1) BOTOX® nanoemulsions, prepared in accordance with Example 1, were injected via intramuscular (IM) injection into the hind leg (gastrocnemius muscle) of Swiss Webster female mice.
2) BOTOX® saline solutions were injected via intramuscular (IM) injection into the hind leg gastrocnemius muscle of Swiss Webster female mice.

The Digit Abduction Score (DAS) assay was used to determine local muscle weakening efficacy (Aoki, 1999). The DAS values were assigned as follows: (0) flat foot, digit spread same as control leg; (1) flat foot, a difference in the width of digit abduction compared to the control leg or two digits touching and the rest spread completely; (2) flat foot, slight space open at tips of all digits or three digits touching; (3) five digits touching if foot is flat, four digits together if foot is curved; (4) curved foot, all five digits touching.

IM injection of BOTOX® nanoemulsion and BOTOX® saline solution were evaluated by DAS seven days under a single-blind protocol. DAS scores of 1-2 were observed for both the botulinum toxin nanoemulsion (3.96 U/5 μl) and botulinum toxin saline solution (3.96 U/5 μl). The control group, which is a blank nanoemulsion, had DAS (0). Each group (botulinum toxin nanoemulsion, saline, and control) was comprised of five (5) animals.

This information proves that microfluidization techniques do not destroy the functional characteristics of botulinum toxin as demonstrated by injection of non-microfluidized botulinum toxin saline solution and that the botulinum toxin nanoemulsions are functionally effective.

Example 3

Muscle Relaxant Effect of Transdermal BOTOX® Nanoemulsions

This example demonstrates the therapeutic efficacy of transdermally applied botulinum nanoemulsions (i.e., for example, a BOTOX® nanoemulsion).

A BOTOX® nanoemulsion (9.9 U/100 μl), prepared in accordance with Example 1, was topically administered to the hind leg gastrocnemius muscle of five (5) Swiss Webster female mice. A control group of five (5) Swiss Webster female mice received an identically prepared nanoemulsion except that BOTOX® was omitted. During the seven days following treatment, DAS scores of 1-2 were observed, scored in accordance with Example 2, for the botulinum toxin nanoemulsion treated group but not in the control group. Aggravation of the skin (e.g. irritation, redness, etc.) was not observed at any time after treatment. The data show that a botulinum toxin nanoemulsion is biologically active upon transdermal administration in a manner similar to conventionally administered botulinum toxin injections.

Example 4

Muscle Relaxant Effects Due to Administration of a Botulinum Nanoemulsion: Controlled Comparison of Standard Injected Botulinum Vs. Topical Botulinum Nanoemulsion in Mice This example provided a controlled experiment to demonstrate that application of an inventive topical botulinum nanoemulsion could induce muscle relaxant effects equivalent to a standard injected botulinum preparation (that was not a nanoemulsion).

Method

Thirty-five female Swiss Webster mice were purchased from Charles River at approximately 20 grams of weight. Upon arrival, all animals were acclimated to their cages for one week (group housed 5 mice per cage per Group as defined below) and provided with standard cage bedding and Purina 5001 chow. After one week, Digit Abduction Scoring (DAS) was used to determine local muscle function following application of a BOTOX® nanoemulsion prepared in accordance with Example 1. In the DAS assay, mice were suspended by the tail briefly (10 seconds) to elicit a characteristic startle response in which the animal extended its hind legs and abducts its hind digits. This assay was performed once a week for 3 weeks.

Three treatment preparations were prepared for three treatment groups of mice: 1) BOTOX® in a saline solution for injection, 2) a nanoemulsion containing BOTOX® and 3) a "blank" nanoemulsion containing all the constituents of the BOTOX® nanoemulsion except the BOTOX® that was also processed through the Microfluidizer® Processor in a manner identical to the nanoemulsion containing BOTOX®.

Treatment Paradigms

Group 1 (IM) 15 Mice were injected with 10 U/5 uL of BOTOX®/kg of body weight that was suspended in a saline solution and then injected into the gastrocnemius muscle of the hind leg of the mice.

Group 2 (Topical) 15 Mice were treated topically with 10 U/100 μl of nanoemulsion of BOTOX®/kg of body weight that was applied to the skin of the mice overlying the gastrocnemius muscle of the hind leg.

Group 3 (Control) 15 Mice were treated topically with blank nanoemulsion containing no BOTOX® that was applied to the skin of the mice overlying the gastrocnemius muscle of the hind leg.

Assessment

One week after injection and/or transdermal application, the DAS assay was used to determine potential local muscle weakening effects of treatment. This assay was performed once a week for the next three weeks. Following injection and/or transdermal application of BOTOX® or a control preparation, the varying degrees of digit abduction was scored on a five-point scale (0=normal to 4=maximal reduction in digit abduction and leg extension) by an observer who was masked to treatment.

Results and Conclusion

At one week after treatment, the group of mice (Group #2) treated with the topical botulinum nanoemulsion preparation achieved a score of 2.8±0.3 on the Aoki scale compared to the control group of mice (Group #3) treated with the blank nanoemulsion that had a score of 0.5±0.3 (P<0.001). By comparison, those mice (Group #1) injected with botulinum in a saline solution had a score of 3.5±0.3. By three weeks after treatment, both the group of mice treated with the topical botulinum nanoemulsion preparation and those mice injected with botulinum in saline had Aoki scores that were at control levels, as expected by the published literature on injected botulinum. (This decrement in Aoki scale in mice has been observed repeatedly with botulinum, which nevertheless has a continued anti-wrinkle effect for several months when used at therapeutic doses in humans.) Furthermore, aggravation of the skin (e.g. irritation, redness, etc.) was not observed at any time after treatment.

In sum, this controlled data suggest strongly that the topical botulinum nanoemulsion preparation delivered a comparable biological effect to injected botulinum.

Example 5

Administration of Botulinum Nanoparticle Composition to a Human Subject to Relieve Wrinkles An inventive topical botulinum nanoemulsion was prepared and applied to a person with significant forehead wrinkles to determine if it could be effective in relaxing the muscles in the forehead that generated those wrinkles (in much the same manner that would be expected from the administration of botulinum suspended in a simple saline solution that was injected into those muscles).

Methods

A botulinum nanoemulsion was made employing the following steps:
1. Stir 800 mg of soybean oil and 800 mg of Tween 80 in a sterile vial for 5 minutes
2. Add 8.4 mL 0.9% saline with 4500 units of an approved botulinum type A toxin pharmaceutical. Stir for 20 minutes
3. Homogenize sample for 1 minute
4. Stir sample for 20 minutes
5. Microfluidize once at 23,000 psi The nanoemulsion was added to an equal volume of skin cream (Base PCCA Vanishing Cream Light) and was vortexed into a uniform cream.

A patient who had significant horizontal wrinkles over his forehead, representing overactivity of his frontalis muscles, was selected for treatment. This patient had had never been treated with a botulinum product or a dermal filler product. The patient was assessed prior to treatment by a board-certified plastic surgeon using a 4-point wrinkle scale, with a score of "1" equal to "no wrinkle" and a score of "4" equal to significant wrinkle. The patient was assessed using this scale when his face was "At Rest" and when he attempted to create maximal wrinkles by contracting his frontalis muscles which was achieved by attempting to maximally elevate his eyebrows ("Maximal Brow Elevation").

This patient had a score of 4 at rest and 4 on maximal brow elevation. He demonstrated excellent mobility of being able to contract the frontalis muscles. The patient was photographed using a digital SLR camera as well as digital video, both At Rest and when asked to perform a Maximal Brow Elevation (FIG. 3A, maximal brow elevation prior to treatment).

The patient was asked not to use any facial make-up or sun-screen on the day of treatment but wash his face prior to coming to the office with Ivory Soap. When at the office, 0.6 CC of the nanoemulsion cream (as prepared in Example 1) was applied to the patient's forehead over the distribution of his frontalis muscles by the plastic surgeon. The cream was applied to the patient's forehead skin by a pipette and rubbed into the skin by the surgeon using his finger (covered by a plastic glove) until the cream was no longer visible by the surgeon. The patient was observed at the physician's office for three hours. He was asked not to touch his forehead for 12 hours and then to wash it off with Ivory Soap and water. The patient was the observed on follow-up after 1 day and then at 1, 2, 4, 8, and 12 weeks. On follow-up visits, the patient's wrinkles At Rest and at Maximal Brow Elevation were assessed by the physician. As well, the physician repeated standardized digital still photographs and video.

Results

By the first week after treatment, the patient was unable to contract his forehead muscles as evidenced by an inability to lift his brow on requested Maximal Brow Elevation (FIG. 3B). His wrinkle score was 2 At Rest and 2 on Maximal Brow Elevation. The physician's clinical assessment was that the treatment had induced a complete paralysis of the treated muscles that was equivalent to treatments he had performed on other patient's using injections of botulinum toxin in a similar treatment area. The patient had a slight restoration of brow mobility by Week 8 but continued to have a significant reduction in his brow mobility at Week 12 of observation.

The patient was able to move his other facial muscles under areas of skin not treated and no side-effects were observed by the plastic surgeon, including no changes to the skin immediately after treatment or in any follow-up visit. Likewise, the patient reported no side-effects, including any changes to his skin (e.g. irritation, redness, etc.) at any time after treatment.

Conclusion

In sum, this experiment strongly suggests that the topical botulinum nanoemulsion preparation delivered a significant biological and clinical effect that was assessed by the plastic surgeon to be comparable in clinical efficacy to what would have been expected for following a standard treatment of injected botulinum (in a simple saline solution) for this patient.

Example 6

Further Botulinum Nanoparticle Composition Formulations

A variety of different botulinum nanoparticle compositions were prepared in accordance with Example 1 except that in some cases, there were differences in the equipment used, the pressure applied, the amount of botulinum added, and the volume of nanoparticle composition prepared, which may account for the variability of the sizes observed. The following average particle size and distributions were observed (Table 3):

TABLE 3

Particle Size Distribution of Microfluidized BOTOX ® Nanoemulsions

| Distribution | Mean Particle Size (nm) | | | | | | |
|---|---|---|---|---|---|---|---|
| Threshold (nm) | 76.8 | 91.5 | 94.2 | 95.3 | 97.9 | 112.4 | Average 95 |
| % above 120 | 36.4 | 48.6 | 47.6 | 54.7 | 50.7 | 53.8 | 49 |
| % above 130 | 21.0 | 37.8 | 35.5 | 37.3 | 40.8 | 45.2 | 36 |
| % above 150 | 9.1 | 27.4 | 24.8 | 20.3 | 31.4 | 36.8 | 25 |
| % above 200 | 2.8 | 16.1 | 10.3 | 1.5 | 15.7 | 21.7 | 11 |
| % above 300 | 0.0 | 0.6 | 4.5 | 0.0 | 3.6 | 9.6 | 3 |

Example 7

Relationship of Pressure Applied to Average Particle Size Achieved

A premix formulation was prepared as described in Example 1 (except for the absence of botulinum toxin) and was split into 4 100 ml aliquots, A-D, each of which was passed through a Microfluidizer® at a different pressure, resulting in a different average particle size, as indicated below in Table 4:

TABLE 4

Particle Sizes of BOTOX ® Nanoemulsions Microfluidized at Different Pressures

| Preparation | Pressure (psi) | Average Particle Size (nm) |
|---|---|---|
| A | 3,500 | 142 nm |
| B | 10,000 | 107 nm |
| C | 17,000 | 94 nm |
| D | 24,000 | 89 nm |

EQUIVALENTS AND SCOPE

The foregoing has been a description of certain non-limiting preferred embodiments of the invention. Those skilled in the art will recognize, or be able to ascertain using no more than routine experimentation, many equivalents to the specific embodiments of the invention described herein. Those of ordinary skill in the art will appreciate that various changes and modifications to this description may be made without departing from the spirit or scope of the present invention, as defined in the following claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise. In addition, the invention encompasses compositions made according to any of the methods for preparing compositions disclosed herein.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Any embodiment, element, feature, application, or aspect of the compositions and/or methods of the invention (e.g., any botulinum toxin, any oil, any surfactant, any dispersion medium, any nanoparticle or composition comprising any nanoparticle, any method of manufacturing nanoparticles, any route or location of administration, any purpose for which a composition is administered, etc.), can be excluded from any one or more claims. For purposes of brevity, all of the embodiments in which one or more elements, features, purposes, or aspects are excluded are not set forth explicitly herein.

We claim:

1. A method of administering botulinum toxin transdermally to a subject, comprising steps of:
   (a) providing:
      (i) a subject;
      (ii) a composition comprising a nanoemulsion characterized in that a majority of its particles have diameters between approximately 10 and approximately 300 nanometers, wherein said nanoemulsion comprises at least one botulinum toxin; and
   (b) administering the composition to the skin of the subject so that the botulinum toxin is delivered into the skin.

2. A method of treating wrinkles, facial lines, and/or neck lines, comprising steps of:
   (a) providing:
      (i) a subject exhibiting symptoms of wrinkles, facial lines, and/or neck lines;
      (ii) a composition comprising a nanoemulsion characterized in that a majority of its particles have diameters between approximately 10 and approximately 300 nanometers, wherein said nanoemulsion comprises at least one botulinum toxin; and
   (b) administering the composition to the skin of the subject such that symptoms are reduced.

3. A method of delaying the onset of the formation of wrinkles, facial lines, and/or neck lines, comprising steps of:

(a) providing:
  (i) a subject not exhibiting symptoms of wrinkles, facial lines, and/or neck lines;
  (ii) a composition comprising a nanoemulsion characterized in that a majority of its particles have diameters between approximately 10 and approximately 300 nanometers, wherein said nanoemulsion comprises at least one botulinum toxin; and,
(b) administering the composition to regions of the skin of the subject that typically develop wrinkles prior to wrinkle formation such that the onset of symptoms is delayed.

4. The method of any one of claims 1-3, wherein the nanoemulsion is characterized in that fewer than 40% of its particles have a diameter in excess of 250 nanometers.

5. The method of any one of claims 1-3, wherein the nanoemulsion is characterized in that its particles have an average particle size of about 10-200 nanometers.

6. The method of claim 1, wherein the nanoemulsion contains an amount of the botulinum toxin such that the botulinum delivered into the skin partially or completely alleviates, ameliorates, relives, inhibits, delays onset of, reduces severity of and/or reduces incidence of one or more symptoms or features of a condition associated with the skin.

7. The method of claim 6, wherein the condition associated with the skin is selected from the group consisting of: facial palsy, facial contracture, hemifacial spasm, blepharospasm, and hyperhidrosis.

8. The method of claim 1, wherein the composition is administered to the skin at a dosage of 1-20,000 units.

9. The method of any one of claims 1-3, wherein the composition is a lotion, ointment, gel, cream, patch, spray, oil or foam.

* * * * *

UNITED STATES PATENT AND TRADEMARK OFFICE
CERTIFICATE OF CORRECTION

| | | |
|---|---|---|
| PATENT NO. | : 8,318,181 B2 | Page 1 of 1 |
| APPLICATION NO. | : 11/607436 | |
| DATED | : November 27, 2012 | |
| INVENTOR(S) | : Edelson et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1491 days.

Signed and Sealed this
Twelfth Day of March, 2013

Teresa Stanek Rea
*Acting Director of the United States Patent and Trademark Office*